(12) United States Patent
Lee

(10) Patent No.: US 10,323,033 B2
(45) Date of Patent: Jun. 18, 2019

(54) IMIDAZO[1,2-A]PYRIDINE-3-CARBOXYLATE DERIVATIVE AND PREPARATION METHOD THEREOF

(71) Applicant: KNU-INDUSTRY COOPERATION FOUNDATION, Chuncheon-si, Gangwon-do (KR)

(72) Inventor: Phil Ho Lee, Chuncheon-si (KR)

(73) Assignee: KNU-INDUSTRY COOPERATION FOUNDATION, Chuncheon-si (KR)

( * ) Notice: Subject to any disclaimer, the term of this patent is extended or adjusted under 35 U.S.C. 154(b) by 0 days.

(21) Appl. No.: 16/004,188

(22) Filed: Jun. 8, 2018

(65) Prior Publication Data

US 2018/0354948 A1 Dec. 13, 2018

(30) Foreign Application Priority Data

Jun. 8, 2017 (KR) .................. 10-2017-0071562

(51) Int. Cl.
*C07D 471/04* (2006.01)
*B01J 31/04* (2006.01)

(52) U.S. Cl.
CPC ............ *C07D 471/04* (2013.01); *B01J 31/04* (2013.01)

(58) Field of Classification Search
None
See application file for complete search history.

(56) References Cited

PUBLICATIONS

Cai et al., "Direct one-pot synthesis of zolimidine pharmaceutical drug and imidazo[1,2-a]pyridine derivatives via I2/CuO-promoted tandem strategy", Chinese Chemical Letters, vol. 26—4 pages, (Jan. 2, 2015).
Huang et al., "Conversion of Pyridine to Imidazo[1,2-a]pyridines by Copper-Catalyzed Aerobic Dehydrogenative Cyclization with Oxime Esters", Orangic Letters, vol. 15, No. 24—4 pages, (Nov. 21, 2013).
Huo et al., "CBr4 Mediated Oxidative C—N Bond Formation: Applied in the Synthesis of Imidazo[1,2-a]pyridines and Imidazo[1,2-a]pyrimidines", Organic Letters, vol. 18—4 pages, (Feb. 16, 2016).
Zeng et al., "Copper(II)/Iron(III) Co-catalyzed Intermolecular Diamination of Alkynes: Facile Synthesis of Imidazopyridines", Organic Letters, vol. 14, No. 17—4 pages, (Aug. 10, 2012).
Zhan et al., "Gold-Catalyzed Synthesis of 3-Acylimidazo[1,2-a]pyridines via Carbene Oxidation", Advanced Synthesis & Catalysis, vol. 357—5 pages, (Dec. 5, 2014).
Zhu et al., "Functionalized heterocyclic scaffolds derived from Morita-Baylis-Hillman Acetates", Chem. Commun., vol. 49—3 pages, (2013).

*Primary Examiner* — Heidi Reese
(74) *Attorney, Agent, or Firm* — Knobbe Martens Olson & Bear LLP

(57) ABSTRACT

Provided are an imidazo[1,2-a]pyridine-3-carboxylate derivative and a preparation method thereof, and more particularly, a method of effectively preparing an imidazo[1,2-a]pyridine-3-carboxylate derivative by performing an aza-[3+2] cycloaddition reaction of a pyridine derivative with an α-diazo oxime ether derivative in the presence of a copper (II) catalyst, and an imidazo[1,2-a]pyridine-3-carboxylate derivative prepared thereby.

9 Claims, No Drawings

IMIDAZO[1,2-A]PYRIDINE-3-CARBOXYLATE DERIVATIVE AND PREPARATION METHOD THEREOF

CROSS-REFERENCE TO RELATED APPLICATIONS

This application claims priority under 35 U.S.C. § 119 to Korean Patent Application No. 10-2017-0071562, filed on Jun. 8, 2017, in the Korean Intellectual Property Office, the disclosure of which is incorporated herein by reference in its entirety.

TECHNICAL FIELD

The following disclosure relates to an imidazo[1,2-a]pyridine-3-carboxylate derivative and a preparation method thereof.

BACKGROUND

A heterocyclic compound containing nitrogen exhibits high physiological activity and pharmacological activity and is very important in biological activity studies and pharmaceutical drug use. In particular, imidazopyridine having pyridine and imidazole residues or moieties constituting a specific skeleton exhibits antibacterial properties and is able to act as an antilipase, a kinase inhibitor and an $H_1$-receptor antagonist. In addition, research of the imidazopyridine is actively underway as a core structure of numerous natural products.

In other words, the imidazopyridine may act as a major building block of Zolpidem which is an insomnia medicine, Alpidem which is an anxiety reliever, Zolimidine which is an anti-ulcer agent, Saripidem which is a sedative, Microprofen which is an analgesic, etc., and a number of researches have been reported on function thereof.

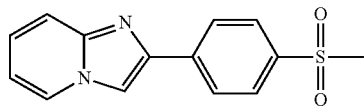

Zolimidine
(gastroprotective drug)

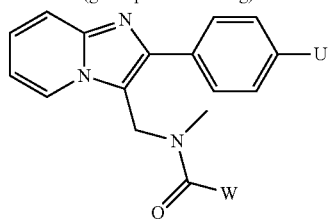

U = Cl, W = $^n$-Pr: Saripidem
U = Et, W = $^i$-Pr: Nezopidem
(sedative or anxiolytic drug)

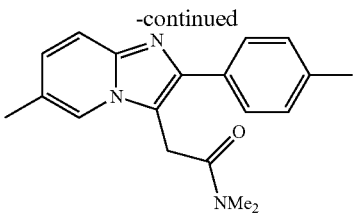

Zolpidem
(insomnia medicine)

Physiologically active imidazopyridine derivate

Thus, methods for synthesizing an N-heterobicyclic compound such as imidazopyridine from starting materials that are readily available in many groups have been reported: a) C. Huo, J. Tang, H. Xie, Y. Wang, J. Dong, *Org. Lett.* 2016, 18, 1016. b) J. Zeng, Y. J. Tan, M. L. Leow, X.-W. Liu, *Org. Lett.* 2012, 14, 4386. c) H. Huang, X. Ji, X. Tang, M. Zhang, S. Li, H. Jiang, *Org. Lett.* 2013, 15, 6254. d) H. Zhu, N. Shao, T. Chen, H. Zou, *Chem. Commun.* 2013, 49, 7738. e) Q. Cai, M.-C. Liu, B.-M. Mao, X. Xie, F.-C. Jia, Y.-P. Zhu, A.-X. Wu, *Chin. Chem. Lett.* 2015, 26, 881. f) H. Zhan, L. Zhao, J. Liao, N. Li, Q. Chen, S. Qiu, H. Cao, *Adv. Synth. Catal.* 2015, 357, 46. The previously reported synthesis method of imidazopyridine includes oxidation of 2-aminopyridine with β-keto ester or 1,3-dione via carbon tetrabromide as an intermediate, carbon-nitrogen (C—N) bond formation reaction, an intermolecular double-amination reaction of 2-aminopyridine and an alkyne under a copper (II) or iron (III) catalyst, a dehydrocyclization reaction of pyridine and oxime ester under copper (I) catalyst, a reaction of 2-aminopyridine with propionaldehyde through an intramolecular cyclization reaction under gold (I) catalyst, a reaction of an activated ketone with 2-aminopyridine, an aromatic cyclization reaction of pyridinium salts and MBHA (Morita-Baylis-Hillman adduct), etc.

However, the previously reported synthesis methods described above have problems such as limitation of introduction of a substituent, difficulty of reaction conditions, and a multi-step reaction step, etc., and thus research into a method of synthesizing an imidazopyridine derivative more efficiently by simpler processes under milder conditions is required.

The disclosure of this section is to provide background of the invention. Applicant notes that this section may contain information available before this application. However, by providing this section, Applicant does not admit that any information contained in this section constitutes prior art.

SUMMARY

An embodiment of the present invention is directed to providing a novel imidazo[1,2-a]pyridine-3-carboxylate derivative having pharmacological activity and physiological activity.

Another embodiment of the present invention is directed to providing a method of effectively preparing an imidazo[1,2-a]pyridine-3-carboxylate derivative by performing an aza-[3+2] cycloaddition reaction of a pyridine derivative with an α-diazo oxime ether derivative in the presence of a copper (II) catalyst.

Still another embodiment of the present invention provides an imidazo[1,2-a]pyridine-3-carboxylate derivative represented by Chemical Formula 1 below.

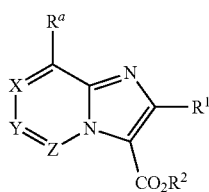

[Chemical Formula 1]

in Chemical Formula 1, $R^1$ is (C1-C10)alkyl, (C6-C12)aryl or (C3-C12)heteroaryl, and the aryl of $R^1$ may be further substituted with one or more selected from the group consisting of (C1-C10)alkyl, halo(C1-C10)alkyl, (C1-C10)alkoxy, halogen, nitro, (C1-C10)alkylcarbonyl, (C1-C10)alkoxycarbonyl and (C6-C12)aryloxy;

$R^2$ is (C1-C10)alkyl or halo(C1-C10)alkyl;

X is $CR^b$ or N;

Y is $CR^c$ or N;

Z is $CR^d$ or N;

$R^a$ to $R^d$ are each independently hydrogen, (C1-C10)alkyl, halo(C1-C10)alkyl, halogen, (C1-C10)alkylcarbonyl, halo(C1-C10)alkylcarbonyl, (C1-10)alkoxycarbonyl, halo(C1-C10)alkoxycarbonyl, (C6-C12)aryl(C1-C10)alkyloxy, (C6-C12)aryl or (C3-C12)heteroaryl, or may be linked to an adjacent substituent to form a fused ring, and the aryl of $R^a$ to $R^d$ and the formed fused ring may be further substituted with one or more selected from (C1-C10)alkyl, halo(C1-C10)alkyl, (C1-C10)alkoxy, (C6-C12)aryl and halogen; and the heteroaryl includes one to four heteroatoms selected from N, O and S.

An embodiment of the present invention is directed to providing a preparation method of an imidazo[1,2-a]pyridine-3-carboxylate derivative including: performing an aza-[3+2] cycloaddition reaction of a pyridine derivative represented by Chemical Formula 6 below with an α-diazo oxime ether derivative represented by Chemical Formula 7 below in the presence of a copper (II) catalyst, thereby preparing an imidazo[1,2-a]pyridine-3-carboxylate derivative represented by Chemical Formula 1 below:

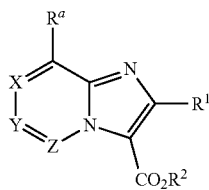

[Chemical Formula 1]

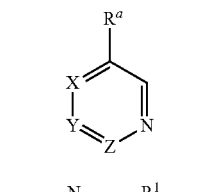

[Chemical Formula 6]

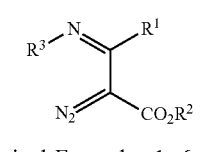

[Chemical Formula 7]

in Chemical Formulas 1, 6, and 7, $R^2$ is (C1-C10)alkyl, (C6-C12)aryl or (C3-C12)heteroaryl, and the aryl of $R^1$ may be further substituted with one or more selected from the group consisting of (C1-C10)alkyl, halo(C1-C10)alkyl, (C1-C10)alkoxy, halogen, nitro, (C1-C10)alkylcarbonyl, (C1-C10)alkoxycarbonyl and (C6-C12)aryloxy;

$R^2$ is (C1-C10)alkyl or halo(C1-C10)alkyl;

$R^3$ is (C1-C10)alkoxy;

X is $CR^b$ or N;

Y is $CR^c$ or N;

Z is $CR^d$ or N;

$R^a$ to $R^d$ are each independently hydrogen, (C1-C10)alkyl, halo(C1-C10)alkyl, halogen, (C1-C10)alkylcarbonyl, halo(C1-C10)alkylcarbonyl, (C1-C10)alkoxycarbonyl, halo(C1-C10)alkoxycarbonyl, (C6-C12)aryl(C1-C10)alkyloxy, (C6-C12)aryl or (C3-C12)heteroaryl, or may be linked to an adjacent substituent to form a fused ring, and the aryl of $R^a$ to $R^d$ and the formed fused ring may be further substituted with one or more selected from (C1-C10)alkyl, halo(C1-C10)alkyl, (C1-C10)alkoxy, (C6-C12)aryl and halogen; and the heteroaryl includes one to four heteroatoms selected from N, O and S.

Another embodiment of the present invention is directed to providing a preparation method of an imidazo[1,2-a]pyridine-3-carboxylate derivative including: performing an aza-[3+2] cycloaddition reaction of a pyridine derivative represented by Chemical Formula 6A below with an α-diazo oxime ether derivative represented by Chemical Formula 7A below in the presence of a copper (II) catalyst in trifluoroethanol, followed by transesterification with trifluoroethanol as a solvent, thereby preparing an imidazo[1,2-a]pyridine-3-carboxylate derivative represented by Chemical Formula 1A below:

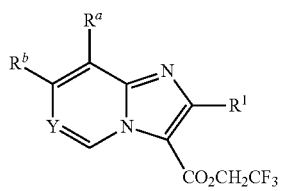

[Chemical Formula 1A]

[Chemical Formula 6A]

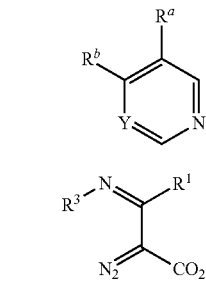

[Chemical Formula 7A]

in Chemical Formulas 1A, 6A, and 7A, $R^1$ is (C1-C10) alkyl or (C6-C12)aryl, and the aryl of $R^1$ may be further substituted with one or more selected from the group consisting of (C1-C10)alkyl, (C1-C10)alkoxy, halogen, nitro and (C1-C10)alkoxycarbonyl;

$R^2$ is (C1-C10)alkyl;

Y is $CR^c$ or N;

$R^3$ is (C1-C10)alkoxy;

$R^a$ is hydrogen, (C1-C10)alkyl or (C6-C12)aryl(C1-C10)alkyloxy;

$R^b$ is (C1-C10)alkyl or (C6-C12)aryl, and the aryl of $R^b$ may be further substituted with one or more selected from (C1-C10)alkyl and halogen; and $R^c$ is hydrogen or (C1-C10)alkyl.

DETAILED DESCRIPTION OF EMBODIMENTS

Hereinafter, embodiments of the present invention will be described in detail.

Here, unless technical and scientific terms used herein are defined otherwise, they have meanings understood by those skilled in the art to which the present invention pertains. In addition, repeated descriptions for technical constitution and function as the same as the related art will be omitted.

One embodiments of the present invention provides an imidazo[1,2-a]pyridine-3-carboxylate derivative represented by Chemical Formula 1 below:

[Chemical Formula 1]

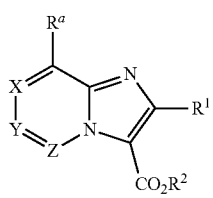

in Chemical Formula 1, $R^1$ is (C1-C10)alkyl, (C6-C12)aryl or (C3-C12)heteroaryl, and the aryl of $R^1$ may be further substituted with one or more selected from the group consisting of (C1-C10) alkyl, halo(C1-C10)alkyl, (C1-C10)alkoxy, halogen, nitro, (C1-C10)alkylcarbonyl, (C1-C10)alkoxycarbonyl and (C6-C12)aryloxy;

$R^2$ is (C1-C10)alkyl or halo(C1-C10)alkyl;

X is $CR^b$ or N;

Y is $CR^c$ or N;

Z is $CR^d$ or N;

$R^a$ to $R^d$ are each independently hydrogen, (C1-C10) alkyl, halo(C1-C10)alkyl, halogen, (C1-C10)alkylcarbonyl, halo(C1-C10)alkylcarbonyl, (C1-C10)alkoxycarbonyl, halo (C1-C10)alkoxycarbonyl, (C6-C12)aryl(C1-C10)alkyloxy, (C6-C12)aryl or (C3-C12)heteroaryl, or may be linked to an adjacent substituent to form a fused ring, and the aryl of $R^a$ to $R^d$ and the formed fused ring may be further substituted with one or more selected from (C1-C10)alkyl, halo(C1-C10)alkyl, (C1-C10)alkoxy, (C6-C12)aryl and halogen; and the heteroaryl includes one to four heteroatoms selected from N, O and S.

The term "alkyl" used herein means a monovalent linear or branched saturated hydrocarbon radical only consisting of carbon atoms and hydrogen atoms. Examples of the alkyl radical may include methyl, ethyl, propyl, isopropyl, butyl, isobutyl, t-butyl, pentyl, hexyl, etc., but the present invention is not limited thereto.

Term "aryl" used herein is an organic radical derived from aromatic hydrocarbon by removal of one hydrogen, and includes a single ring system or a fused ring system including 4 to 7 ring atoms, preferably, 5 or 6 ring atoms in each ring, and even includes a form in which a plurality of aryls are connected by a single bond. Specific examples of aryl may include phenyl, naphthyl, biphenyl, anthryl, fluorenyl, indenyl, etc., but the present invention is not limited thereto.

In embodiments of the present invention,

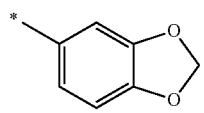

is also included in the aryl.

Term "halo" or "halogen" used herein means a fluorine atom, a chlorine atom, a bromine atom or an iodine atom.

Term "haloalkyl" used herein means that at least one hydrogen present on the alkyl is substituted with a halogen.

Term "alkoxy" used herein means —O-alkyl radical, wherein the 'alkyl' is the same as described above. Examples of the alkoxy radical include methoxy, ethoxy, isopropoxy, butoxy, isobutoxy, t-butoxy, etc., but the present invention is not limited thereto.

Term "heteroaryl" used herein, which means an aryl group including 1 to 4 heteroatoms selected from N, O, and S as an aromatic ring framework atom and carbon as the remaining aromatic ring framework atom, is a 5- to 6-membered monocyclic heteroaryl and a polycyclic heteroaryl condensed with at least one benzene ring. In addition, the heteroaryl in embodiments of the present invention includes even a form in which one or more heteroaryls are connected by a single bond. As a specific example, the heteroaryl includes monocyclic heteroaryl such as furyl, thiophenyl, pyrrolyl, imidazolyl, pyrazolyl, thiazolyl, isothiazolyl, isoxazolyl, oxazolyl, pyridyl, or the like, polycyclic heteroaryl such as benzofuranyl, dibenzofuranyl, dibenzothiopheyl, benzothiophenyl, isobenzofuranyl, benzoimidazolyl, benzothiazolyl, benzoisothiazolyl, benzoisoxazolyl, benzoxazolyl, quinolyl, isoquinolyl, carbazolyl, or the like, but is not limited thereto.

In the imidazo[1,2-a]pyridine-3-carboxylate derivative according to an embodiment of the present invention, the imidazo[1,2-a]pyridine-3-carboxylate derivative may be selected from derivatives represented by Chemical Formulas 2 to 5 below:

[Chemical Formula 2]

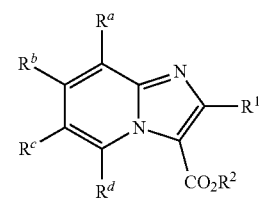

[Chemical Formula 3]

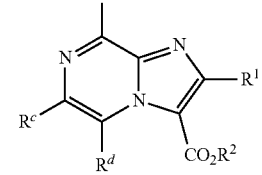

[Chemical Formula 4]

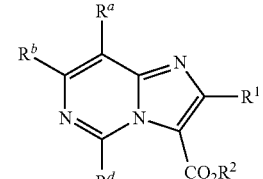

[Chemical Formula 5]

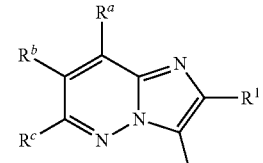

in Chemical Formulas 2 to 5 above, $R^1$ and $R^2$ are the same as defined in Chemical Formula 1 above;

$R^a$ to $R^d$ are each independently hydrogen, (C1-C10)alkyl, halo(C1-C10)alkyl, halogen, (C1-C10)alkylcarbonyl, halo(C1-C10)alkylcarbonyl, (C1-C10)alkoxycarbonyl, halo(C1-C10)alkoxycarbonyl, (C6-C12)aryl(C1-C10)alkyloxy, (C6-C12)aryl or (C3-C12)heteroaryl, or may be linked to an adjacent substituent via —$CR^{11}$=$CR^{12}$—$CR^{13}$=$CR^{14}$— to form a fused ring;

the aryl of $R^a$ to $R^d$ may be further substituted with one or more selected from (C1-C10)alkyl, halo(C1-C10)alkyl and halogen; and $R^{11}$ to $R^{14}$ are each independently hydrogen, (C1-C10)alkyl, halo(C1-C10)alkyl, (C1-C10)alkoxy, (C6-C12)aryl, or halogen.

In the imidazo[1,2-a]pyridine-3-carboxylate derivative according to an embodiment of the present invention, $R^1$ is (C1-C7)alkyl, (C6-C12)aryl or (C3-C12)heteroaryl, and the aryl of $R^1$ may be further substituted with one or more selected from the group consisting of (C1-C7)alkyl, (C1-C7)alkoxy, halogen, nitro and (C1-C10)alkoxycarbonyl, and $R_2$ is (C1-C7)alkyl or halo(C1-C7)alkyl; and $R^a$ to $R^d$ are each independently hydrogen, (C1-C7)alkyl, halo(C1-C7)alkyl, halogen, (C1-C7)alkylcarbonyl, halo(C1-C7)alkylcarbonyl, (C1-C7)alkoxycarbonyl, halo(C1-C7)alkoxycarbonyl, (C6-C12)aryl(C1-C7)alkyloxy, or (C6-C12)aryl, or may be linked to an adjacent substituent via

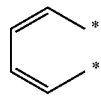

to form a fused ring, and the aryl of $R^a$ to $R^d$ may be further substituted with one or more selected from (C1-C10)alkyl, halo(C1-C10)alkyl, and halogen.

In the imidazo[1,2-a]pyridine-3-carboxylate derivative according to an embodiment of the present invention, $R^1$ is methyl, ethyl, propyl, butyl, pentyl, hexyl, phenyl, biphenyl, naphthyl, thiophenyl, furyl, pyrrolyl, pyridyl, pyrimidinyl, quinolyl, triazolyl, oxazolyl, triazolyl or

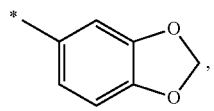

the phenyl, biphenyl or naphthyl of $R^1$ may be further substituted with one or more substituents selected from the group consisting of methyl, ethyl, propyl, butyl, pentyl, hexyl, methoxy, ethoxy, propoxy, butoxy, pentyloxy, hexyloxy, chloro, bromo, fluoro, iodo, nitro, methoxycarbonyl, ethoxycarbonyl or butoxycarbonyl; $R^2$ is methyl, ethyl, propyl, butyl, trifluoromethyl, trifluoroethyl, trifluoropropyl, perfluoroethyl, perfluoropropyl, perfluorobutyl; $R^a$ to $R^d$ are each independently hydrogen, methyl, ethyl, propyl, butyl, pentyl, hexyl, chloro, bromo, fluoro, iodo, methylcarbonyl, ethylcarbonyl, propylcarbonyl, butylcarbonyl, trifluoromethylcarbonyl, trifluoroethylcarbonyl, trifluoropropylcarbonyl, perfluoroethylcarbonyl, methoxycarbonyl, ethoxycarbonyl, propoxycarbonyl, butoxycarbonyl, trifluoromethoxycarbonyl, trifluoroethoxycarbonyl, trifluoropropoxycarbonyl, perfluoroethoxycarbonyl, benzyloxy, phenyl, biphenyl or naphthyl, or may be linked to an adjacent substituent via

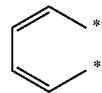

to form a fused ring; and the phenyl, biphenyl or naphthyl of $R^a$ to $R^d$ may be further substituted with one or more substituents selected from the group consisting of methyl, ethyl, propyl, butyl, pentyl, hexyl, chloro, bromo, fluoro and iodo.

More specifically, the imidazo[1,2-a]pyridine-3-carboxylate derivative according to an embodiment of the present invention may be selected from the following derivatives, but is not limited thereto:

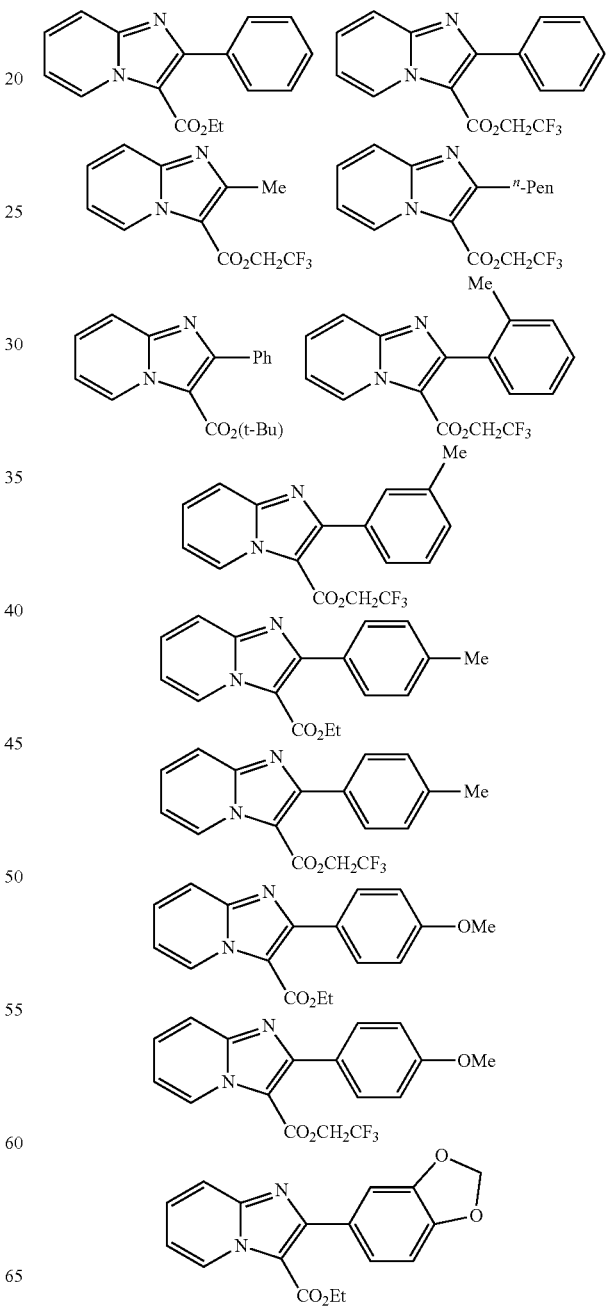

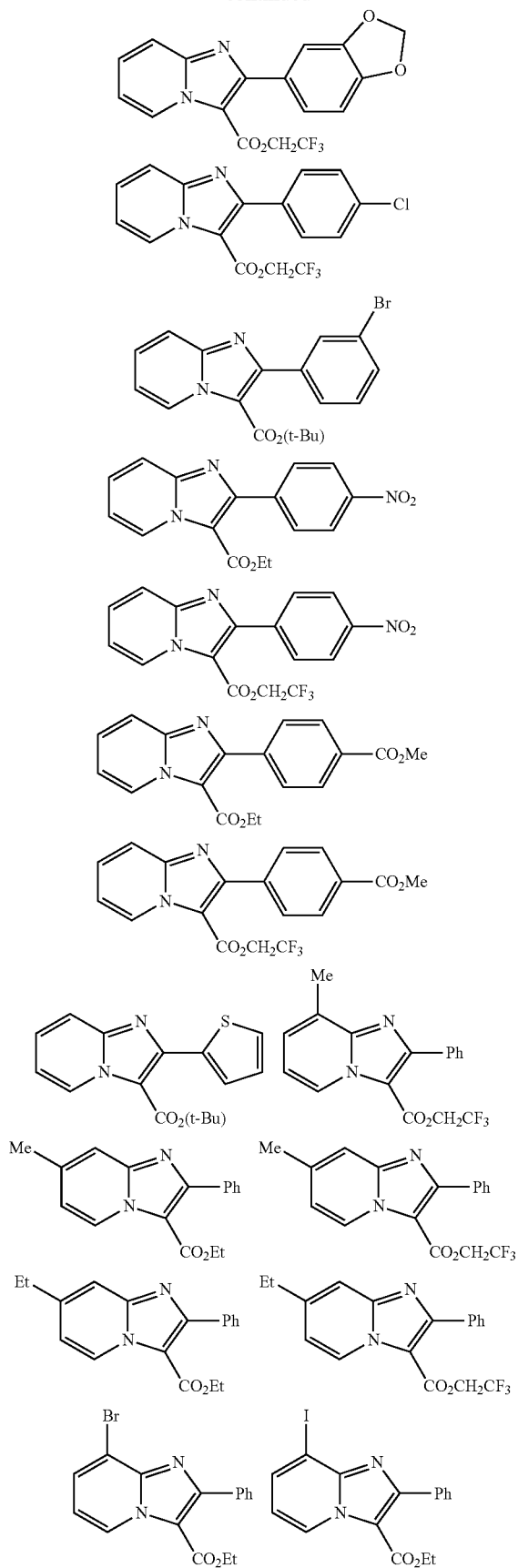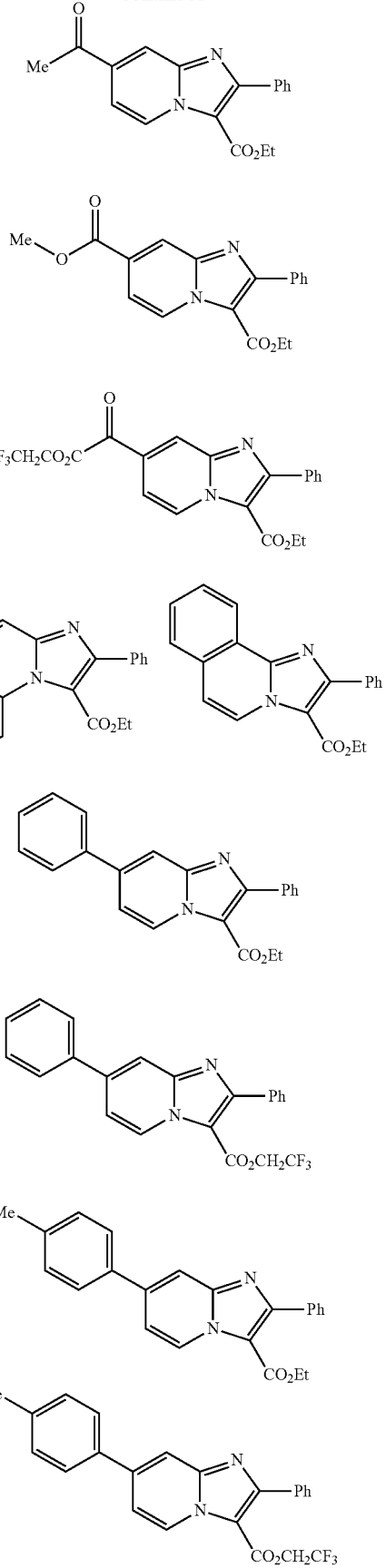

-continued

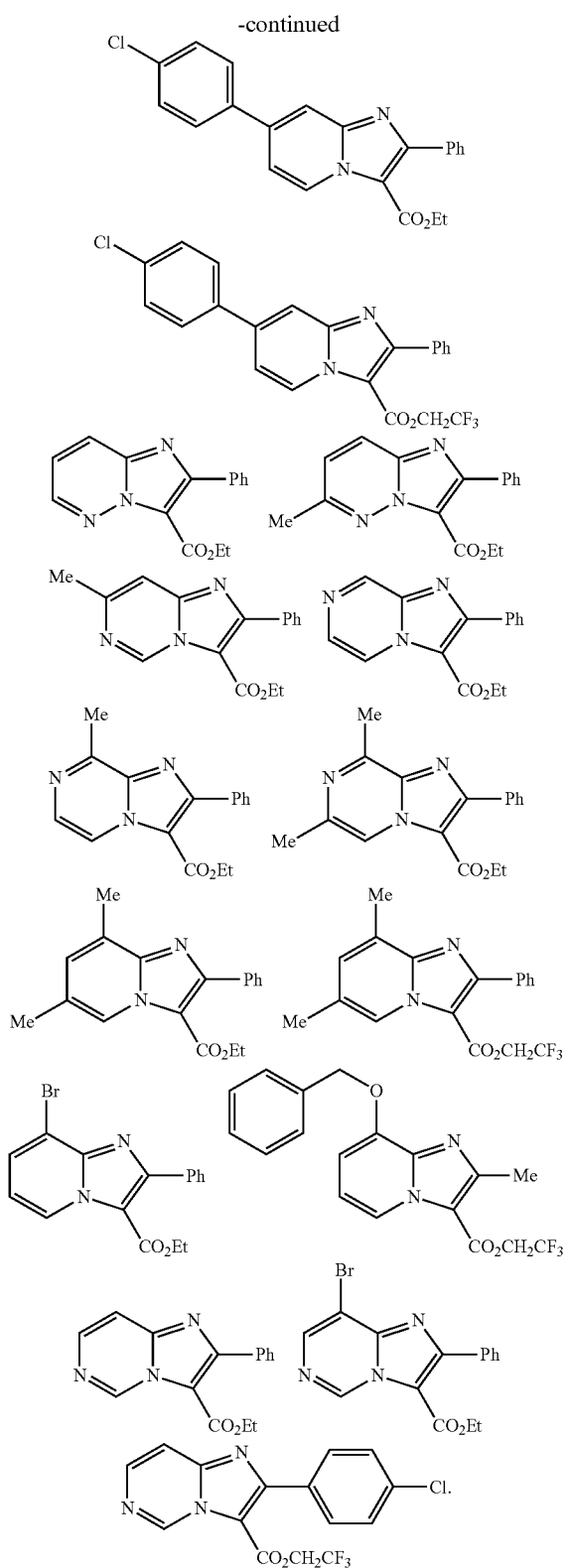

Hereinafter, a preparation method of an imidazo[1,2-a]pyridine-3-carboxylate derivative according to embodiments of the present invention will be described in detail.

One embodiments of the present invention provides a preparation method of an imidazo[1,2-a]pyridine-3-carboxylate derivative including: performing an aza-[3+2] cycloaddition reaction of a pyridine derivative represented by Chemical Formula 6 below with an α-diazo oxime ether derivative represented by Chemical Formula 7 below in the presence of a copper (II) catalyst, thereby preparing an imidazo[1,2-a]pyridine-3-carboxylate derivative represented by Chemical Formula 1 below:

[Chemical Formula 1]

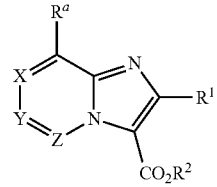

[Chemical Formula 6]

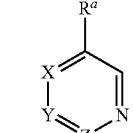

[Chemical Formula 7]

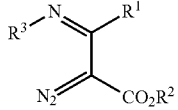

in Chemical Formulas 1, 6, and 7, $R^1$ is (C1-C10)alkyl, (C6-C12)aryl or (C3-C12)heteroaryl, and the aryl of $R^1$ may be further substituted with one or more selected from the group consisting of (C1-C10) alkyl, halo(C1-C10)alkyl, (C1-C10)alkoxy, halogen, nitro, (C1-C10)alkylcarbonyl, (C1-C10)alkoxycarbonyl and (C6-C12)aryloxy;

$R^2$ is (C1-C10)alkyl or halo(C1-C10)alkyl;

$R^3$ is (C1-C10)alkoxy;

X is $CR^b$ or N;

Y is $CR^c$ or N;

Z is $CR^d$ or N;

$R^a$ to $R^d$ are each independently hydrogen, (C1-C10) alkyl, halo(C1-C10)alkyl, halogen, (C1-C10)alkylcarbonyl, halo(C1-C10)alkylcarbonyl, (C1-C10)alkoxycarbonyl, halo (C1-C10)alkoxycarbonyl, (C6-C12)aryl(C1-C10)alkyloxy, (C6-C12)aryl or (C3-C12)heteroaryl, or may be linked to an adjacent substituent to form a fused ring, and the aryl of $R^a$ to $R^d$ and the formed fused ring may be further substituted with one or more selected from (C1-C10)alkyl, halo(C1-C10)alkyl, (C1-C10)alkoxy, (C6-C12)aryl and halogen; and the heteroaryl includes one to four heteroatoms selected from N, O and S.

The preparation method of the imidazo[1,2-a]pyridine-3-carboxylate derivative represented by Chemical Formula 1 above according to embodiments of the present invention is a copper (II)-catalyzed aza-[3+2] cycloaddition reaction of a pyridine derivative with an α-diazo oxime ether derivative, synthesized the imidazo[1,2-a]pyridine-3-carboxylate derivative through molecular nitrogen release and alcohol removal by simple processes and under mild conditions. This method is a very effective method for preparing a wide range of N-heterobicyclic derivatives such as imidazopyridazine, imidazopyrimidine, and imidazopyrazine.

In an embodiment of the present invention, the imidazo [1,2-a]pyridine-3-carboxylate derivative represented by Chemical Formula 1 is prepared by performing an aza-[3+2] cycloaddition reaction of a pyridine derivative represented by Chemical Formula 6 below with an α-diazo oxime ether derivative represented by Chemical Formula 7 below in the presence of a copper (II) catalyst, followed by the release of molecular nitrogen and elimination of alcohol, as shown in Reaction Scheme 1 below:

[Reaction Scheme 1]

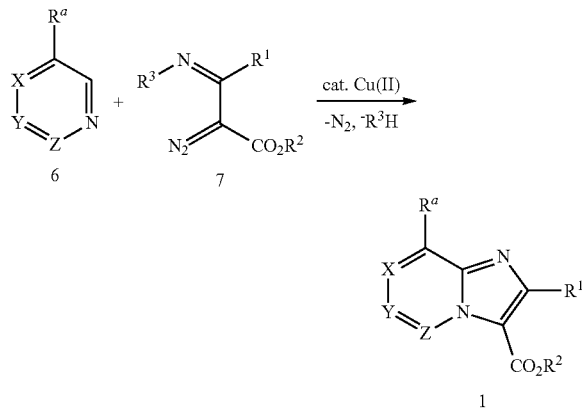

in Reaction Scheme 1, $R^1$ to $R^3$, X, Y, Z and $R^a$ are the same as defined in Chemical Formula 1 above.

In the preparation method of the imidazo[1,2-a]pyridine-3-carboxylate derivative according to an embodiment of the present invention, the reaction may be performed under an organic solvent, and the organic solvent is not limited as long as it is capable of dissolving the reaction material. The organic solvent is preferably selected from the group consisting of trifluoroethanol, 1,4-dioxane, acetonitrile, toluene, tetrahydrofuran, dimethylformamide, dichloromethane, dichloroethane, N,N-dimethylformamide, hexane, benzene, xylene, chlorobenzene, hexafluorobenzene, octafluorotoluene, tetrabutylalcohol, methanol, ethanol, and a mixture thereof, and more preferably, trifluoroethanol.

In addition, one embodiment of the present invention provides a preparation method of an imidazo[1,2-a]pyridine-3-carboxylate derivative including: performing an aza-[3+2] cycloaddition reaction of a pyridine derivative represented by Chemical Formula 6A below with an α-diazo oxime ether derivative represented by Chemical Formula 7A below in the presence of a copper (II) catalyst in trifluoroethanol, followed by transesterification with trifluoroethanol as a solvent, thereby preparing an imidazo[1,2-a]pyridine-3-carboxylate derivative represented by Chemical Formula 1A below:

[Chemical Formula 1A]

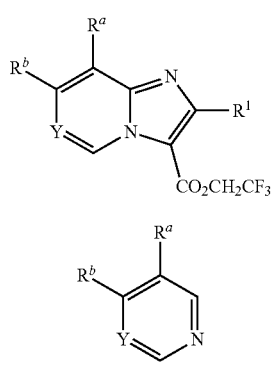

[Chemical Formula 6A]

[Chemical Formula 7A]

in Chemical Formulas 1A, 6A, and 7A, $R^1$ is (C1-C10)alkyl or (C6-C12)aryl, and the aryl of $R^1$ may be further substituted with one or more selected from the group consisting of (C1-C10)alkyl, (C1-C10)alkoxy, halogen, nitro and (C1-C10)alkoxycarbonyl;

$R^2$ is (C1-C10) alkyl;

Y is $CR^c$ or N;

$R^3$ is (C1-C10)alkoxy;

$R^a$ is hydrogen, (C1-C10)alkyl or (C6-C12)aryl(C1-C10) alkyloxy;

$R^b$ is (C1-C10) alkyl or (C6-C12) aryl, and the aryl of $R^b$ may be further substituted with one or more selected from (C1-C10)alkyl and halogen; and $R^c$ is hydrogen or (C1-C10)alkyl.

In the preparation method of an imidazo[1,2-a]pyridine-3-carboxylate derivative represented by Chemical Formula 1A according to embodiments of the present invention, the imidazo[1,2-a]pyridine-3-carboxylate derivative (Chemical Formula 1A) was synthesized via the release of molecular nitrogen and elimination of alcohol by simple processes and under mild conditions, by performing a copper (II)-catalyzed aza-[3+2] cycloaddition reaction of a pyridine derivative (Chemical Formula 6A) with an α-diazo oxime ether derivative (Chemical Formula 7A) under a trifluoroethanol solvent, followed by transesterification with trifluoroethanol as a solvent. This method is a very effective method for preparing an imidazopyridazine derivative.

In an embodiment of the present invention, the imidazo[1,2-a]pyridine-3-carboxylate derivative represented by Chemical Formula 1A is prepared by performing an aza-[3+2] cycloaddition reaction of a pyridine derivative represented by Chemical Formula 6A below with an α-diazo oxime ether derivative represented by Chemical Formula 7A below in the presence of a copper (II) catalyst in trifluoroethanol, followed by transesterification with trifluoroethanol as a solvent, as shown in Reaction Scheme 2 below:

[Reaction Scheme 2]

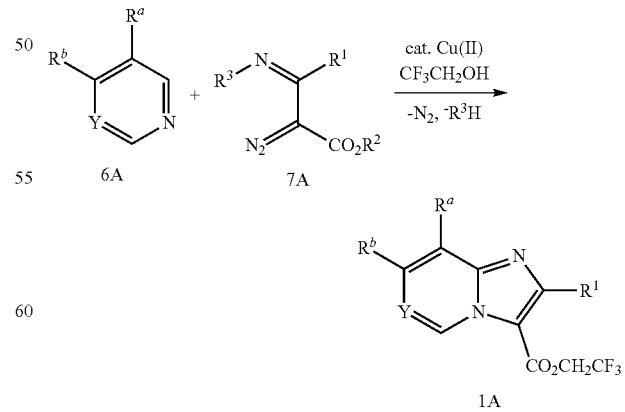

in Reaction Scheme 2, Y, $R^1$ to $R^3$, $R^a$ and $R^b$ are the same as defined in Chemical Formula 1A above.

In the preparation method of the imidazo[1,2-a]pyridine-3-carboxylate derivative according to an embodiment of the present invention, the copper (II) catalyst may be one or a mixture of two or more selected from the group consisting of Cu(OAc)$_2$[Copper(II) acetate], Cu(OTf)$_2$[Copper(II) triflate], Cu(acac)$_2$[Copper(II) acetylacetonate], Cu(tfacac)$_2$[Copper(II) trifluoroacetylacetonate], and Cu(hfacac)$_2$[Copper(II) hexafluoroacetylacetonate]. Among them, Cu(hfacac)$_2$ is preferably selected as the copper (II) catalyst.

In the preparation method of the imidazo[1,2-a]pyridine-3-carboxylate derivative according to an embodiment of the present invention, an amount of the copper (II) catalyst may be 1 to 20 mol %, and preferably 5 to 10 mol % with respect to the pyridine derivative represented by Chemical Formula 6 or Chemical Formula 6A. When the copper (II) catalyst is used in the above-described range, the reaction may occur well, and when the copper (II) catalyst is used out of the range, yield and economical efficiency may be lowered.

In the preparation method of the imidazo[1,2-a]pyridine-3-carboxylate derivative according to an embodiment of the present invention, a used amount of the α-diazo oxime ether derivative represented by Chemical Formula 7 or Chemical Formula 7A may be to 3 equivalents, and the most preferably 2.0 to 2.5 equivalents, with respect to the pyridine derivative represented by Chemical Formula 6 or Chemical Formula 6A.

In the preparation method of the imidazo[1,2-a]pyridine-3-carboxylate derivative according to an embodiment of the present invention, a reaction temperature is not limited as long as the temperature is generally used in organic synthesis, and the temperature may vary according to reaction time, and amounts of reaction materials and starting materials. The reaction may be performed at a reaction temperature of 50 to 150° C., and preferably, 80 to 100° C. in order to prevent deterioration of the reaction yield caused by excessively increased reaction time or occurrence of side products.

The reaction time may vary depending on the kind of the reaction material, the type of the solvent, and the amount of the solvent. After confirming that the starting material is completely consumed through TLC, or the like, the reaction is completed. After the reaction is completed, the solvent is distilled under reduced pressure, and a target material may be separated and purified by general methods such as column chromatography, and the like.

Hereinafter, the present disclosure will be described in detail with reference to Examples. These Examples are provided to help understand the present invention, and the scope of the present disclosure is not construed to be limited to these Examples.

EXAMPLE

Preparation of imidazo[1,2-a]pyridine-3-carboxylate Derivative 1

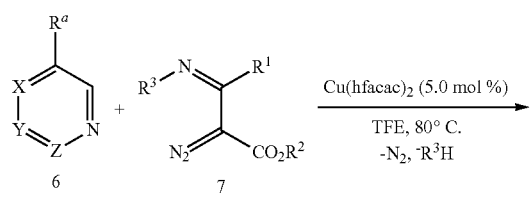

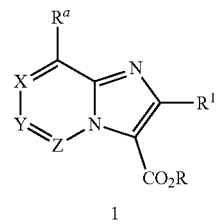

(R = R$^2$ or -CH$_2$CF$_3$)

To a dried test tube, Cu(hfacac)$_2$ (5.0 mol % or 10.0 mol %) and trifluoroethanol (1.0 mL) were added, a mixed solution of an α-diazo oxime ether derivative 7 (0.4 mmol or 0.5 mmol) and trifluoroethanol (1.0 mL) was added thereto, and a pyridine derivative 6 (0.2 mmol) was added thereto. The reaction mixture was stirred at 80° C. or 90° C. for 3 hours, 8 hours or 12 hours, and then passed through a silica gel filter pad (eluent: CH$_2$Cl$_2$) to remove Cu(hfacac)$_2$. The obtained filtrate was concentrated under reduced pressure, and the residue was purified by silica gel flash column chromatography to obtain an imidazo[1,2-a]pyridine-3-carboxylate derivative 1 as a target compound.

Various imidazo[1,2-a]pyridine-3-carboxylate derivatives 1 were prepared using the methods described above.

Example 1

Preparation of ethyl 2-phenylimidazo[1,2-a]pyridine-3-carboxylate

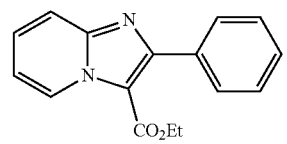 [SMILES: CCOC(=O)c1c(-c2ccccc2)nc2ccccn12]

Cu(hfacac)$_2$ (5.0 mol %), α-diazo oxime ether derivative 7 (0.4 mmol), reaction temperature of 80° C., and reaction time for 3 hours Yield: 22.9 mg (43%); White solid; mp 53-55° C.; R$_f$=0.2 (EtOAc:DCM:Hexane=1:10:10); $^1$H NMR (400 MHz, CDCl$_3$) δ 9.41 (td, J=1.1 Hz, 7.0 Hz, 1H), 7.78-7.72 (m, 3H), 7.45-7.40 (m, 4H), 7.02 (dt, J=1.2 Hz, 10.4 Hz, 1H), 4.30 (q, J=7.1 Hz, 2H), 1.22 (t, J=7.1 Hz, 3H); $^{13}$C$^1$H NMR (100 MHz, CDCl$_3$) δ 161.2, 153.7, 147.2, 134.6, 130.3, 128.8, 128.4, 128.0, 127.8, 127.6, 117.6, 114.2, 60.5, 14.1; IR (KBr) 3058, 2979, 2929, 1684, 1400, 1225, 1155, 1050 cm$^{-1}$; HRMS (EI) calcd for C$_{16}$H$_{14}$N$_2$O$_2$ 266.1055, found 266.1051.

Example 2

Preparation of 2,2,2-trifluoroethyl 2-phenylimidazo[1,2-a]pyridine-3-carboxylate

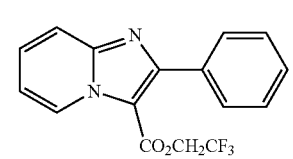

Cu(hfacac)$_2$ (5.0 mol %), α-diazo oxime ether derivative 7 (0.4 mmol), reaction temperature of 80° C., and reaction time for 3 hours Yield: 35.2 mg (55%); White solid; mp 99-101° C.; R$_f$=0.15 (EtOAc:DCM:Hexane=1:10:10); $^1$H NMR (400 MHz, CDCl$_3$) δ 9.39 (td, J=1.1 Hz, 7.0 Hz, 1H), 7.79 (td, J=1.1 Hz, 9.0 Hz, 1H), 7.74-7.72 (m, 2H), 7.54-7.49 (m, 1H), 7.47-7.43 (m, 3H), 7.10 (dt, J=1.3 Hz, 10.4 Hz, 1H), 4.62 (q, J=8.4 Hz, 2H); $^{13}$C$^1$H NMR (100 MHz, CDCl$_3$) δ 159.0, 155.4, 147.8, 133.9, 130.0, 129.0, 128.8, 128.4, 128.0, 127.8, 122.9 (J=277.6 Hz), 117.7, 114.7, 110.4, 59.8 (J=36.9 Hz); $^{19}$F NMR δ −73.1 ppm; IR (KBr) 3058, 2970, 1699, 1494, 1414, 1281, 1148 cm$^{-1}$; HRMS (EI) calcd for C$_{16}$H$_{11}$F$_3$N$_2$O$_2$ 320.0773, found 320.0773.

Example 3

Preparation of 2,2,2-trifluoroethyl 2-methylimidazo[1,2-a]pyridine-3-carboxylate

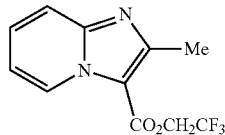

Cu(hfacac)$_2$ (5.0 mol %), α-diazo oxime ether derivative 7 (0.4 mmol), reaction temperature of 80° C., and reaction time for 3 hours Yield: 49.6 mg (96%); White solid; mp 100-102° C.; R$_f$=0.2 (EtOAc:DCM:Hexane=1:10:10); $^1$H NMR (400 MHz, CDCl$_3$) δ 9.24 (d, J=6.9 Hz, 1H), 7.66 (d, J=8.9 Hz, 1H), 7.47-7.43 (m, 1H), 7.03 (dt, J=1.0 Hz, 10.4 Hz, 1H), 4.76 (q, J=8.4 Hz, 2H), 2.74 (s, 3H); $^{13}$C$^1$H NMR (100 MHz, CDCl$_3$) δ 159.3, 154.7, 147.8, 128.6, 128.1, 123.3 (J=277.2 Hz), 117.0, 114.4, 111.3, 60.0 (J=36.7 Hz) 16.9; $^{19}$F NMR δ −73.7 ppm; IR (KBr) 3036, 2963, 2926, 1698, 1425, 1278, 1155 cm$^{-1}$; HRMS (EI) calcd for C$_{11}$H$_9$F$_3$N$_2$O$_2$ 258.0616, found 258.0613.

Example 4

Preparation of 2,2,2-trifluoroethyl 2-pentylimidazo[1,2-a]pyridine-3-carboxylate

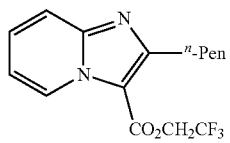

Cu(hfacac)$_2$ (5.0 mol %), α-diazo oxime ether derivative 7 (0.4 mmol), reaction temperature of 80° C., and reaction time for 3 hours Yield: 37.5 mg (77%); White solid; mp 71-73° C.; R$_f$=0.3 (EtOAc:DCM:Hexane=1:10:10); White solid; 1H NMR (400 MHz, CDCl3) d 9.27 (dd, J=0.7 Hz, 6.9 Hz, 1H), 7.68 (dd, J=0.7 Hz, 8.9 Hz, 1H), 7.45 (t, J=7.9 Hz, 1H), 7.04 (t, J=6.9 Hz, 1H), 4.75 (q, J=8.4 Hz, 2H), 3.09 (t, J=7.9 Hz, 2H), 1.82-1.74 (m, 2H), 1.45-1.32 (m, 4H) 0.91 (t, J=6.86 Hz, 3H); $^{13}$C NMR (100 MHz, CDCl$_3$) d 159.3, 159.1, 148.0, 128.6, 128.2, 123.4 (J=277.2 Hz), 117.2, 114.3, 110.8, 60.1 (J=36.7 Hz), 32.0, 30.7, 29.5, 22.6, 14.1; $^{19}$F NMR δ −73.5 ppm; IR (KBr) 2959, 2923, 2861, 1702, 1415, 1335, 1278, 1170, 1080 cm$^{-1}$; HRMS (EI) calcd for C$_{15}$H$_{17}$F$_3$N$_2$O$_2$ 314.1242, found 314.1239.

Example 5

Preparation of tert-butyl 2-phenylimidazo[1,2-a]pyridine-3-carboxylate

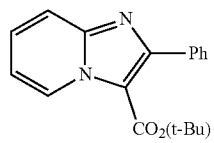

Cu(hfacac)$_2$ (5.0 mol %), α-diazo oxime ether derivative 7 (0.4 mmol), reaction temperature of 80° C., and reaction time for 3 hours Yield: 34.2 mg (58%); Colorless oil; R$_f$=0.3 (EtOAc:DCM:Hexane=1:10:10); $^1$H NMR (400 MHz, CDCl$_3$) δ 9.41 (td, J=1.1 Hz, 7.0 Hz, 1H), 7.72-7.69 (m, 3H), 7.45-7.38 (m, 4H), 6.99 (dt, 1.2 Hz, 10.4 Hz, 1H), 1.43 (s. 9H); $^{13}$C$^1$H NMR (100 MHz, CDCl$_3$) δ 160.7, 153.2, 146.8, 135.0, 130.2, 128.4, 128.3, 127.6, 127.6, 117.5, 113.9, 113.2, 82.0, 28.3; IR (KBr) 3069, 2978, 2930, 1682, 1496, 1391, 1338, 1227, 1150 cm$^{-1}$; HRMS (EI) calcd for C$_{18}$H$_{18}$N$_2$O$_2$ 294.1368, found 294.1368.

Example 6

Preparation of 2,2,2-trifluoroethyl 2-(o-tolyl)imidazo[1,2-a]pyridine-3-carboxylate

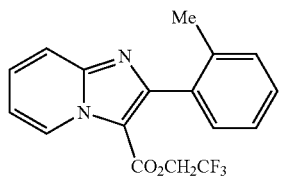

Cu(hfacac)$_2$ (5.0 mol %), α-diazo oxime ether derivative 7 (0.4 mmol), reaction temperature of 90° C., and reaction time for 8 hours Yield: 49.5 mg (74%); Colorless oil; R$_f$=0.3 (EtOAc:DCM:Hexane=1:20:20); $^1$H NMR (400 MHz, CDCl$_3$) δ 9.37 (d, J=6.9 Hz, 1H), 7.78 (d, J=9.0 Hz, 1H), 7.55-7.50 (m, 1H), 7.34-7.21 (m, 4H), 7.13 (t, J=10.4 Hz, 1H), 4.49 (q, J=8.4 Hz, 2H), 2.21 (s, 3H); $^{13}$C1H NMR (100 MHz, CDCl$_3$) δ 159.1, 155.6, 147.9, 136.6, 134.2, 129.8, 129.6, 128.8, 128.7, 128.3, 125.2, 122.8 (J=277.5 Hz), 117.9, 114.8, 111.6, 59.9 (J=36.9 Hz) 19.9; $^{19}$F NMR δ −73.8 ppm; IR (KBr) 3028, 2968, 2927, 1702, 1494, 1414, 1280, 1152 cm-1; HRMS (EI) calcd for C$_{17}$H$_{13}$F$_3$N$_2$O$_2$ 334.0929, found 334.0927.

Example 7

Preparation of 2,2,2-trifluoroethyl 2-(m-tolyl)imidazo[1,2-a]pyridine-3-carboxylate

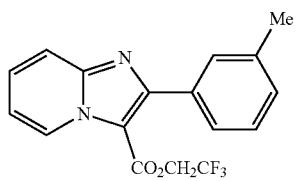

Cu(hfacac)$_2$ (5.0 mol %), α-diazo oxime ether derivative 7 (0.4 mmol), reaction temperature of 90° C., and reaction time for 8 hours Yield: 65.8 mg (98%); White solid; mp 75-77° C.; R$_f$=0.3 (EtOAc:DCM:Hexane=1:20:20); $^1$H NMR (400 MHz, CDCl$_3$) δ 9.39 (td, J=1.1 Hz, 7.0 Hz, 1H), 7.78 (td, J=1.1 Hz, 8.9 Hz, 1H), 7.55-7.49 (m, 3H), 7.34 (t, J=7.6 Hz, 1H), 7.25 (d, J=7.0 Hz, 1H), 7.09 (dt, J=1.3 Hz, 10.4 Hz, 1H), 4.62 (q, J=8.5 Hz, 2H), 2.41 (s, 3H); $^{13}$C$^1$H NMR (100 MHz, CDCl$_3$) δ 159.3, 155.7, 148.0, 137.6, 133.9, 130.7, 129.9, 128.9, 128.6, 127.8, 127.3, 123.1 (J=277.5 Hz), 117.8, 114.8, 110.4, 59.9 (J=36.9 Hz), 21.4; $^{19}$F NMR δ −73.1 ppm; IR (KBr) 3054, 2978, 2930, 1685, 1496, 1384, 1227, 1150 cm$^{-1}$; HRMS (EI) calcd for C$_{17}$H$_{13}$F$_3$N$_2$O$_2$ 334.0929, found 334.0930.

Example 8

Preparation of ethyl 2-(p-tolyl)imidazo[1,2-a]pyridine-3-carboxylate

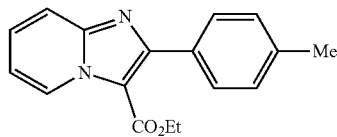 [SMILES: CCOC(=O)c1c(-c2ccc(C)cc2)nc2ccccn12]

Cu(hfacac)$_2$ (5.0 mol %), α-diazo oxime ether derivative 7 (0.4 mmol), reaction temperature of 80° C., and reaction time for 3 hours Yield: 11.8 mg (21%); White solid; R$_f$=0.3 (EtOAc:DCM:Hexane=1:20:20); $^1$H NMR (400 MHz, CDCl$_3$) δ 9.41 (td, J=1.1, 7.0 Hz, 1H), 7.73 (td, J=1.1 Hz, 8.9 Hz, 1H), 7.68 (dd, J=1.7 Hz, 6.4 Hz, 2H), 7.45-7.40 (m, 1H), 7.24 (dd, J=0.6 Hz, 8.5 Hz, 2H), 7.02 (dt, J=1.3 Hz, 10.4 Hz, 1H), 4.33 (q, J=7.1 Hz, 2H), 2.42 (s, 3H), 1.26 (t, J=7.1 Hz, 3H); $^{13}$C$^1$H NMR (100 MHz, CDCl$_3$) δ 161.4, 153.9, 147.2, 138.7, 131.6, 130.2, 128.5, 128.4, 127.9, 117.6, 114.0, 111.9, 60.5, 21.5, 14.2

Example 9

Preparation of 2,2,2-trifluoroethyl 2-(p-tolyl)imidazo[1,2-a]pyridine-3-carboxylate

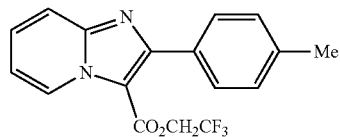

Cu(hfacac)$_2$ (5.0 mol %), α-diazo oxime ether derivative 7 (0.4 mmol), reaction temperature of 80° C., and reaction time for 3 hours Yield: 42.1 mg (63%); White solid; mp 154-157° C.; R$_f$=0.35 (EtOAc:DCM:Hexane=1:20:20); $^1$H NMR (400 MHz, CDCl$_3$) δ 9.37 (d, J=7.0 Hz, 1H), 7.77 (d, J=8.9 Hz, 1H), 7.65 (d, J=8.1 Hz, 2H), 7.52-7.48 (m, 1H), 7.25 (d, J=6.5 Hz, 2H), 7.09 (dt, J=1.2 Hz, 10.4 Hz, 1H), 4.63 (q, J=8.5 Hz, 2H), 2.42 (s, 3H); $^{13}$C$^1$H NMR (100 MHz, CDCl$_3$) δ 159.2, 155.7, 148.0, 139.1, 131.0, 130.1, 128.8, 128.6, 123.1 (J=277.8Hz), 117.8, 114.7, 110.4, 59.8 (J=36.9 Hz), 21.5; $^{19}$F NMR δ −73.0 ppm; IR (KBr) 2980, 2924, 1683, 1497, 1404, 1336, 1223, 1155 cm$^{-1}$; HRMS (EI) calcd for C$_{17}$H$_{13}$F$_3$N$_2$O$_2$ 334.0929, found 334.0930.

Example 10

Preparation of 2,2,2-trifluoroethyl 2-(4-methoxyphenyl)imidazo[1,2-a]pyridine-3-carboxylate and ethyl 2-(4-methoxyphenyl)imidazo[1,2-a]pyridine-3-carboxylate

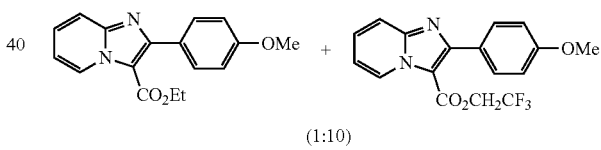

(1:10)

Cu(hfacac)$_2$ (5.0 mol %), α-diazo oxime ether derivative 7 (0.4 mmol), reaction temperature of 80° C., and reaction time for 3 hours

[2,2,2-trifluoroethyl 2-(4-methoxyphenyl)imidazo[1,2-a]pyridine-3-carboxylate (major isomer)] Yield: 61.3 mg (81%); White solid; mp 92-94° C.; R$_f$=0.3 (EtOAc:DCM:Hexane=1:20:20); $^1$H NMR (400 MHz, CDCl$_3$) δ 9.36 (d, J=7.0 Hz, 1H), 7.72 (dd, J=2.1 Hz, J=6.8 Hz, 1H), 7.51-7.47 (m, 1H), 7.07 (dd, J=1.1 Hz, 10.4 Hz, 1H), 6.98(dd, J=2.1 Hz, J=6.8 Hz 2H), 4.64 (q, J=8.5 Hz, 2H), 3.87 (s, 3H); $^{13}$C$^1$H NMR (100 MHz, CDCl$_3$) δ 160.5, 159.2, 155.4, 148.0, 131.6, 128.9, 128.6, 126.3, 123.1 (J=277.7 Hz), 117.7, 114.6, 113.4, 110.1, 59.9 (J=36.9 Hz), 55.5; $^{19}$F NMR δ −73.0 ppm; IR (KBr) 2967, 2839, 1697, 1612, 1484, 1417, 1387, 1281, 1250, 1176 cm$^{-1}$; HRMS (EI) calcd for C$_{17}$H$_{13}$F$_3$N$_2$O$_3$ 350.0878, found 350.0880.

[Ethyl 2-(4-methoxyphenyl)imidazo[1,2-a]pyridine-3-carboxylate (minor isomer)] Yield: 5.3 mg (8%); White solid; mp 92-94° C.; R$_f$=0.3 (EtOAc:DCM:Hexane=1:20: 20); $^1$H NMR (400 MHz, CDCl$_3$) δ 9.40 (d, J=7.0 Hz, 1H), 7.76-7.70 (m, 3H), 7.43-7.39 (m, 1H), 7.02-7.00 (m, 1H), 7.00-6.95 (m, 2H), 4.33 (q, J=7.1 Hz, 2H), 3.87 (s, 3H), 1.27

(t, J=7.2 Hz, 3H); NMR (100 MHz, CDCl$_3$) δ 161.4, 160.2, 153.6, 131.8, 128.5, 128.0, 127.0, 117.4, 114.0, 113.4, 60.5, 14.3; HRMS (EI) calcd for C$_{17}$H$_{16}$N$_2$O$_3$ 296.1161, found 296.1162.

Example 11

Preparation of mixture of 2,2,2-trifluoroethyl 2-(benzo[d][1,3]dioxol-5-yl)imidazo[1,2-a]pyridine-3-carboxylate and ethyl 2-(benzo[d][1,3]dioxol-5-yl)imidazo[1,2-a]pyridine-3-carboxylate

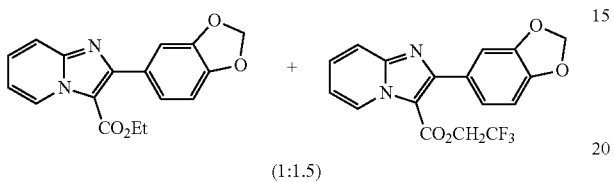

(1:1.5)

Cu(hfacac)$_2$ (5.0 mol %), α-diazo oxime ether derivative 7 (0.4 mmol), reaction temperature of 80° C., and reaction time for 3 hours Yield: 20.5 mg (33%), 36.4 mg (50%); White solid; mp 69-71° C.; R$_f$=0.2 (EtOAc:DCM:Hexane=1:3:3); major isomer: $^1$H NMR (400 MHz, CDCl$_3$) δ 9.34 (td, J=1.1 Hz, 7.0 Hz, 1H), 7.73 (td, J=1.1 Hz, 9.0 Hz, 1H), 7.50-7.46 (m, 1H), 7.34-7.23 (m, 2H), 7.06 (dt, J=1.2 Hz, 10.4 Hz, 1H), 6.90 (d, J=8.1 Hz, 1H), 5.99 (s, 2H), 4.65 (q, J=8.5 Hz, 2H); minor isomer: $^1$H NMR (400 MHz, CDCl$_3$) δ 9.39 (td, J=1.1 Hz, 7.0 Hz, 1H), 7.70 (td, J=1.1 Hz, 9.0 Hz, 1H), 7.43-7.39 (m, 1H), 7.34-7.23 (m, 2H), 7.00 (dt, J=1.3 Hz, 10.4 Hz, 1H), 6.90 (d, J=8.0 Hz, 1H), 6.01 (s, 2H), 4.34 (q, J=7.1 Hz, 2H), 1.27 (t, J=7.1 Hz, 3H); mixture: $^{13}$C$^1$H NMR (100 MHz, CDCl$_3$) δ 161.1, 159.0, 155.1, 153.2, 148.5, 148.1, 147.8, 147.3, 147.0, 128.9, 128.5, 128.4, 128.3, 128.0, 127.7, 124.5, 123.1 (J=277.6 Hz), 117.6, 117.7, 114.4, 114.0, 111.7, 110.9, 110.6, 110.2, 107.9, 107.7, 101.30, 101.26, 101.2, 60.5, 59.9 (J=36.8 Hz), 14.1; $^{19}$F NMR δ −73.1 ppm; IR (KBr) 3051, 2978, 2898, 1696, 1472, 1394, 1342, 1242, 1170, 1040 cm$^{-1}$; HRMS (EI) calcd for C$_{17}$H$_{11}$F$_3$N$_2$O$_4$ 364.0671, C$_{17}$H$_{14}$N$_2$O$_4$ 310.0954, found 364.0671, 310.0953.

Example 12

Preparation of 2,2,2-trifluoroethyl 2-(4-chlorophenyl)imidazo[1,2-a]pyridine-3-carboxylate

Cu(hfacac)$_2$ (5.0 mol %), α-diazo oxime ether derivative 7 (0.4 mmol), reaction temperature of 80° C., and reaction time for 3 hours Yield: 63.3 mg (89%); White solid; mp 118-120° C.; R$_f$=0.3 (EtOAc:DCM:Hexane=1:20:20); $^1$H NMR (400 MHz, CDCl$_3$) δ 9.38 (d, J=7.0 Hz, 1H), 7.78 (d, 9.0 Hz 1H), 7.69 (dd, J=1.9 Hz, 6.6 Hz, 2H), 7.55-7.51 (m, 1H), 7.43 (dd, J=1.9 Hz, 6.7 Hz, 2H), 7.12 (dt, J=1.1 Hz, 10.4 Hz, 1H), 4.63 (q, J=8.4 Hz, 2H); $^{13}$C$^1$H NMR (100 MHz, CDCl$_3$) δ 159.0, 154.3, 148.0, 135.3, 132.5, 131.5, 129.2, 128.6, 128.2, 123.0 (J=277.6 Hz), 117.9, 115.0, 110.6, 60.0 (J=36.9 Hz); $^{19}$F NMR δ −73.1 ppm; IR (KBr) 2970, 2917, 1700, 1409, 1384, 1336, 1280, 1147 cm$^{-1}$; HRMS (EI) calcd for C$_{16}$H$_{10}$ClF$_3$N$_2$O$_2$ 354.0383, found 354.0386.

Example 13

Preparation of tert-butyl 2-(3-bromophenyl)imidazo[1,2-a]pyridine-3-carboxylate

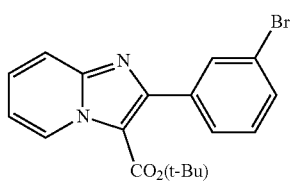

Cu(hfacac)$_2$ (5.0 mol %), α-diazo oxime ether derivative 7 (0.4 mmol), reaction temperature of 80° C., and reaction time for 3 hours Yield: 66.4 mg (89%); Colorless oil; R$_f$=0.4 (EtOAc:DCM:Hexane=1:10:10); $^1$H NMR (400 MHz, CDCl$_3$) δ 9.42 (td, J=1.1 Hz, 7.0 Hz, 1H), 7.86 (t, J=1.7 Hz, 1H), 7.72 (td, J=1.0 Hz, 8.9 Hz, 1H), 7.68 (td, J=1.3 Hz, 7.7 Hz, 1H), 7.53 (qd, J=1.0 Hz, 8.0 Hz, 1H), 7.45-7.41 (m, 1H) 7.31 (t, J=7.9 Hz, 1H), 7.02 (dt, J=1.2 Hz, 10.4 Hz, 1H), 1.47 (s, 9H); $^{13}$C$^1$H NMR (100 MHz, CDCl$_3$) δ 160.5, 151.3, 146.9, 137.1, 133.5, 131.4, 129.3, 128.8, 128.4, 128.0, 121.5, 117.6, 114.2, 113.3, 82.3, 28.4; IR (KBr) 2978, 2930, 1684, 1496, 1384, 1227, 1150 cm$^{-1}$; HRMS (EI) calcd for C$_{18}$H$_{17}$$^{79}$BrN$_2$O$_2$ 372.0473, C$_{18}$H$_{17}$$^{81}$BrN$_2$O$_2$, 374.0455 found 372.0470, 374.0461.

Example 14

Preparation of ethyl 2-(4-nitrophenyl)imidazo[1,2-a]pyridine-3-carboxylate

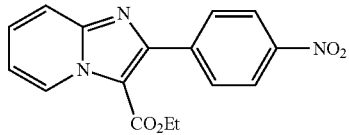 [SMILES: CCOC(=O)c1c(-c2ccc([N+](=O)[O-])cc2)nc2ccccn12]

Cu(hfacac)$_2$ (5.0 mol %), α-diazo oxime ether derivative 7 (0.4 mmol), reaction temperature of 80° C., and reaction time for 3 hours Yield: 37.4 mg (60%); White solid; mp 174-176° C.; R$_f$=0.15 (EtOAc:Hexane=1:5); $^1$H NMR (400 MHz, CDCl$_3$) δ 9.43 (td, J=1.1 Hz, 7.0 Hz, 1H), 8.31 (dd, J=2.0 Hz, 6.9 Hz, 2H), 7.97 (dd, J=2.0 Hz, 6.9 Hz, 2H), 7.77 (td, J=1.1 Hz, 9.0 Hz, 1H), 7.52-7.48 (m, 1H), 7.10 (dt, J=1.2 Hz, 10.4 Hz, 1H), 4.35 (q, J=7.1 Hz, 2H), 1.25 (t, J=7.1 Hz, 3H); $^{13}$C$^1$H NMR (100 MHz, CDCl$_3$) δ 160.6, 150.9, 148.0, 147.4, 141.2, 131.4, 128.6, 128.5, 122.9, 117.9, 114.8, 112.7, 61.0, 14.2; IR (KBr) 2997, 2918, 1687, 1516, 1380, 1344, 1225, 1169 cm$^{-1}$; HRMS (EI) calcd for C$_{16}$H$_{13}$N$_3$O$_4$ 311.0906 found 311.0904.

Example 15

Preparation of 2,2,2-trifluoroethyl 2-(4-nitrophenyl)imidazo[1,2-a]pyridine-3-carboxylate

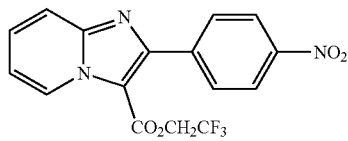

Cu(hfacac)$_2$ (5.0 mol %), α-diazo oxime ether derivative 7 (0.4 mmol), reaction temperature of 80° C., and reaction time for 3 hours Yield: 13.2 mg (18%); White solid; mp 71-73° C.; $R_f$=0.1 (EtOAc:Hexane=1:5); $^1$H NMR (400 MHz, CDCl$_3$) δ 9.40 (td, J=1.0 Hz, 7.0 Hz, 1H), 8.32 (dd, J=1.9 Hz, 6.9 Hz, 2H), 7.92 (dd, J=2.0 Hz, 6.9 Hz, 2H), 7.82 (td, J=1.1 Hz, 9.0 Hz, 1H), 7.60-7.56 (m, 1H), 7.18 (dt, J=1.2 Hz, 10.4 Hz, 1H), 4.63 (q, J=8.4 Hz, 2H); $^{13}$C$^1$H NMR (100 MHz, CDCl$_3$) δ 158.6, 152.7, 148.3, 148.1, 140.6, 131.2, 129.6, 128.6, 123.1, 122.9 (J=277.3 Hz), 118.1, 115.5, 111.1, 60.1 (J=36.9 Hz); $^{19}$F NMR δ −73.1 ppm; IR (KBr) 3083, 2917, 2849, 1705, 1519, 1413, 1348 cm$^{-1}$; HRMS (EI) calcd for C$_{16}$H$_{10}$F$_3$N$_3$O$_4$ 365.0623 found 365.0622.

Example 16

Preparation of 2,2,2-trifluoroethyl 2-(4-methoxyphenyl)imidazo[1,2-a]pyridine-3-carboxylate and ethyl 2-(4-methoxyphenyl)imidazo[1,2-a]pyridine-3-carboxylate

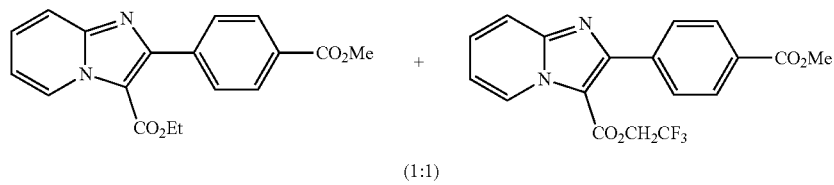

(1:1)

Cu(hfacac)$_2$ (5.0 mol %), α-diazo oxime ether derivative 7 (0.4 mmol), reaction temperature of 80° C., and reaction time for 3 hours Yield: 26.6 mg (41%), 31.8 mg (42%); White solid; mp 92-94° C.; $R_f$=0.3 (EtOAc:DCM:Hexane=1:20:20)

[2,2,2-trifluoroethyl 2-(4-methoxyphenyl)imidazo[1,2-a]pyridine-3-carboxylate (major isomer)]: $^1$H NMR (400 MHz, CDCl$_3$) δ 9.39 (d, J=0.9 Hz, J=7.0 Hz, 1H), 8.14-8.12 (m, 2H), 7.86-7.82 (m, 3H), 7.55-7.51 (m, 1H), 7.06 (t, J=6.9 Hz, 1H), 4.62 (q, J=8.4 Hz, 2H), 3.96 (s, 3H); $^{13}$C$^1$H NMR (100 MHz, CDCl$_3$) δ 160.5, 159.2, 155.4, 148.0, 131.6, 128.9, 128.6, 126.3, 123.1 (J=277.7 Hz), 117.7, 114.6, 113.4, 110.1, 59.9 (J=36.9 Hz), 55.5; $^{19}$F NMR δ −73.0 ppm; IR (KBr) 2967, 2839, 1697, 1612, 1484, 1417, 1387, 1281, 1250, 1176 cm$^{-1}$; HRMS (EI) calcd for C$_{18}$H$_{13}$F$_3$N$_2$O$_4$ 378.0827, found 378.0831.

[Ethyl 2-(4-methoxyphenyl)imidazo[1,2-a]pyridine-3-carboxylate (minor isomer)] $^1$H NMR (400 MHz, CDCl$_3$) δ 9.43 (dd, J=0.9 Hz, J=7.0 Hz, 1H), 8.12-8.11 (m, 2H), 7.80-7.74 (m, 3H), 7.48-7.44 (m, 1H), 7.13 (t, J=6.9 Hz, 1H), 4.31 (q, J=7.1 Hz, 2H), 3.96 (s, 3H), 1.22 (t, J=7.1 Hz, 3H); $^{13}$C$^1$H NMR (100 MHz, CDCl$_3$) δ 161.4, 160.2, 153.6, 131.8, 128.5, 128.0, 127.0, 117.4, 114.0, 113.4, 60.5, 14.3; HRMS (EI) calcd for C$_{18}$H$_{16}$N$_2$O$_4$ 324.1110, found 324.1108.

Example 17

Preparation of tert-butyl 2-(thiophen-2-yl)imidazo[1,2-a]pyridine-3-carboxylate

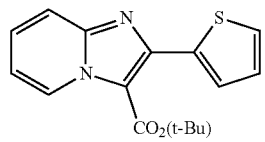

Cu(hfacac)$_2$ (5.0 mol %), α-diazo oxime ether derivative 7 (0.4 mmol), reaction temperature of 80° C., and reaction time for 3 hours Yield: 25.9 mg (43%); Brown solid; mp 116-119° C.; $R_f$=0.3 (EtOAc:DCM:Hexane=1:20:20); $^1$H NMR (400 MHz, CDCl$_3$) δ 9.32 (td, J=1.1 Hz, 7.2 Hz, 1H), 7.93 (dd, J=1.1 Hz, 3.7 Hz, 1H), 7.68 (d, J=9.0 Hz, 1H), 7.44 (dd, J=1.1 Hz, 5.1 Hz, 1H), 7.40-7.36 (m, 1H), 7.12 (dd, J=3.7 Hz, 5.1 Hz, 1H), 6.95 (dt, J=1.2 Hz, 10.4 Hz, 1H), 1.63 (s, 9H); $^{13}$C$^1$H NMR (100 MHz, CDCl$_3$) δ 160.5, 146.7, 146.4, 136.8, 129.9, 129.0, 128.6, 127.9, 127.8, 127.3, 117.4, 113.9, 82.8, 28.7; IR (KBr) 2963, 2928, 2855, 1725, 1680, 1497, 1381, 1342, 1132 cm$^{-1}$; HRMS (EI) calcd for C$_{16}$H$_{16}$N$_2$O$_2$S 300.0932, found 300.0930.

Example 18

Preparation of 2,2,2-trifluoroethyl 8-methyl-2-phenylimidazo[1,2-a]pyridine-3-carboxylate

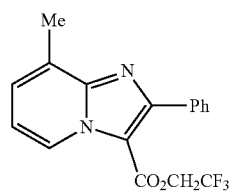

Cu(hfacac)$_2$ (5.0 mol %), α-diazo oxime ether derivative 7 (0.4 mmol), reaction temperature of 90° C., and reaction time for 8 hours Yield: 56.4 mg (84%); White solid; mp 110-113° C.; $R_f$=0.3 (EtOAc:DCM:Hexane=1:10:10); $^1$H NMR (400

MHz, CDCl₃) δ 9.24 (d, J=6.8 Hz, 1H), 7.72-7.70 (m, 2H), 7.45-7.42 (m, 3H), 7.30 (td, J=1.0 Hz, 7.0 Hz, 1H), 7.01 (t, J=7.0 Hz, 1H), 4.59 (q, J=8.4 Hz, 2H), 2.70 (s, 3H); $^{13}C^{1}H$ NMR (100 MHz, CDCl₃) δ 159.3, 155.1, 148.2, 134.4, 130.2, 129.0, 127.9, 127.8, 126.2, 123.0 (J=266.8 Hz), 114.8, 110.9, 59.8 (J=36.8 Hz), 17.2; $^{19}F$ NMR δ −73.2 ppm; IR (KBr) 3033, 2970, 1698, 1490, 1381, 1281, 1234, 1169, 1108 cm⁻¹; HRMS (EI) calcd for $C_{17}H_{13}F_3N_2O_2$ 344.0929, found 344.0927.

Example 19

Preparation of ethyl 7-methyl-2-phenylimidazo[1,2-a]pyridine-3-carboxylate

Cu(hfacac)₂ (5.0 mol %), α-diazo oxime ether derivative 7 (0.4 mmol), reaction temperature of 80° C., and reaction time for 3 hours Yield: 17.4 mg (31%); White solid; mp 48-51° C.; $R_f$=0.3 (EtOAc:DCM:Hexane=1:10:10); ¹H NMR (400 MHz, CDCl₃) δ 9.28 (d, J=7.1 Hz, 1H), 7.77-7.75 (m, 2H), 7.49 (s, 1H), 7.44-7.41 (m, 3H), 6.87 (dd, J=1.7 Hz, 7.1 Hz, 1H), 4.30 (q, J=7.1 Hz, 2H), 2.48 (s, 3H), 1.22 (t, J=7.1 Hz, 3H); $^{13}C^{1}H$ NMR (100 MHz, CDCl₃) δ 161.3, 153.9, 147.7, 139.4, 134.8, 130.3, 130.2, 128.7, 127.8, 127.7, 116.7, 116.2, 60.5, 21.6, 14.1; IR (KBr) 3058, 2979, 2929, 1684, 1400, 1225, 1155, 1050 cm⁻¹; HRMS (EI) calcd for $C_{17}H_{16}N_2O_2$ 280.1212, found 280.1213.

Example 20

Preparation of 2,2,2-trifluoroethyl 7-methyl-2-phenylimidazo[1,2-a]pyridine-3-carboxylate

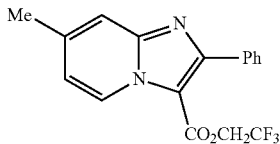

Cu(hfacac)₂ (5.0 mol %), α-diazo oxime ether derivative 7 (0.4 mmol), reaction temperature of 80° C., and reaction time for 3 hours Yield: 33.5 mg (50%); White solid; mp 108-111° C.; $R_f$=0.2 (EtOAc:DCM:Hexane=1:10:10); ¹H NMR (400 MHz, CDCl₃) δ 9.24 (d, J=7.1 Hz, 1H), 7.73-7.71 (m, 2H), 7.53 (s, 1H), 7.45-7.43 (m, 3H), 6.94 (dd, J=1.7 Hz, 7.1 Hz, 1H), 4.60 (q, J=8.5 Hz, 2H), 2.50 (s, 3H); $^{13}C^{1}H$ NMR (100 MHz, CDCl₃) δ 159.2, 155.7, 148.4, 140.5, 134.1, 130.1, 129.1, 127.9, 127.7, 123.1 (J=277.7 Hz), 117.3, 116.5, 110.1, 59.8 (J=36.9 Hz), 21.6; $^{19}F$ NMR δ −73.1 ppm; IR (KBr) 3036, 2969, 2925, 1693, 1413, 1281, 1169, 1069 cm⁻¹; HRMS (EI) calcd for $C_{17}H_{13}F_3N_2O_2$ 334.0929, found 334.0926.

Example 21

Preparation of 2,2,2-trifluoroethyl 7-ethyl-2-phenylimidazo[1,2-a]pyridine-3-carboxylate and ethyl 7-ethyl-2-phenylimidazo[1,2-a]pyridine-3-carboxylate

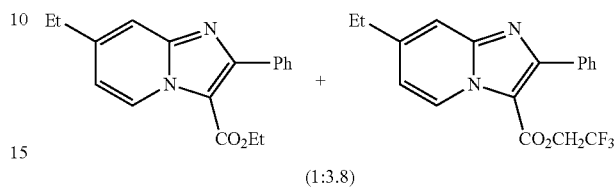

(1:3.8)

Cu(hfacac)₂ (5.0 mol %), α-diazo oxime ether derivative 7 (0.4 mmol), reaction temperature of 80° C., and reaction time for 3 hours

[2,2,2-trifluoroethyl 7-ethyl-2-phenylimidazo[1,2-a]pyridine-3-carboxylate (major isomer)] Yield: 41.1 mg (59%); White solid; mp 119-121° C.; $R_f$=0.4 (EtOAc:DCM:Hexane=1:20:20); ¹H NMR (400 MHz, CDCl₃) δ 9.25 (d, J=7.1 Hz, 1H), 7.74-7.71 (m, 2H), 7.56 (s, 1H), 7.44-7.42 (m, 3H), 6.97 (d, J=7.1 Hz, 1H), 4.60 (q, J=8.5 Hz, 2H), 2.80 (q, J=7.6 Hz, 2H), 1.33 (t, J=7.6 Hz, 3H); $^{13}C^{1}H$ NMR (100 MHz, CDCl₃) δ 159.2, 155.8, 148.6, 146.5, 134.2, 130.3, 130.1, 129.0, 127.9, 127.7, 120.1 (J=295.8 Hz), 116.3, 115.1, 59.8 (J=37.0 Hz), 28.6, 14.4; $^{19}F$ NMR δ −73.1 ppm; IR (KBr) 3138, 3062, 2971, 2931, 1692, 1406, 1283, 1163 cm⁻¹; HRMS (EI) calcd for $C_{18}H_{15}F_3N_2O_2$ 348.1086, found 348.1085.

[Ethyl 7-ethyl-2-phenylimidazo[1,2-a]pyridine-3-carboxylate (minor isomer)] Yield: 9.1 mg (15%); White solid; mp 119-121° C.; $R_f$=0.4 (EtOAc:DCM:Hexane=1:20:20); ¹H NMR (400 MHz, CDCl₃) δ 9.30 (d, J=7.2 Hz, 1H), 7.78-7.75 (m, 2H), 7.52 (s, 1H), 7.44-7.42 (m, 3H), 6.91 (d, J=6.8 Hz, 1H), 4.30 (q, J=7.1 Hz, 2H), 2.76 (q, J=8.0 Hz, 2H), 1.22 (t, J=7.1 Hz, 3H), 1.22 (t, J=7.1 Hz, 3H); HRMS (EI) calcd for $C_{18}H_{18}N_2O_2$ 294.1368, found 294.1368.

Example 22

Preparation of ethyl 8-bromo-2-phenylimidazo[1,2-a]pyridine-3-carboxylate

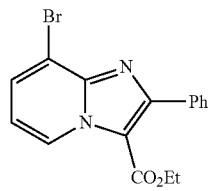 [SMILES: CCOC(=O)c1c(-c2ccccc2)nc2c(Br)cccn12]

Cu(hfacac)₂ (5.0 mol %), α-diazo oxime ether derivative 7 (0.4 mmol), reaction temperature of 80° C., and reaction time for 3 hours Yield: 53.9 mg (78%); White solid; mp 109-110° C.; $R_f$=0.5 (EtOAc:DCM:Hexane=1:20:20); ¹H NMR (400 MHz, CDCl₃) δ 9.43 (dd, J=1.0 Hz, 7.0 Hz, 1H), 7.77-7.75 (m, 2H), 7.69 (dd, J=1.0 Hz, 7.4 Hz, 1H), 7.44-7.42 (m, 3H), 6.92 (t, J=7.2 Hz, 1H), 4.30 (q, J=7.1 Hz, 2H), 1.20 (t, J=7.1 Hz, 3H); $^{13}C^{1}H$ NMR (100 MHz, CDCl₃) δ 161.2, 154.0, 145.1, 134.2, 130.5, 130.4, 128.9, 127.7, 114.2, 113.8, 111.7, 60.9, 14.0; IR (KBr) 2980, 1685, 1490, 1402, 1322, 1239, 1156 cm$^{-1}$; HRMS (EI) calcd for $C_{16}H_{13}{}^{79}BrN_2O_2$ 344.0160, $C_{16}H_{13}{}^{81}BrN_2O_2$ 346.0142, found 344.0158, 346.0140.

Example 23

Preparation of ethyl 8-iodo-2-phenylimidazo[1,2-a]pyridine-3-carboxylate

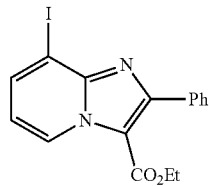 [SMILES: CCOC(=O)c1c(-c2ccccc2)nc2c(I)cccn12]

Cu(hfacac)$_2$ (5.0 mol %), α-diazo oxime ether derivative 7 (0.4 mmol), reaction temperature of 80° C., and reaction time for 3 hours Yield: 58.8 mg (75%); White solid; mp 109-110° C.; $R_f$=0.5 (EtOAc:DCM:Hexane=1:20:20); $^1$H NMR (400 MHz, CDCl$_3$) δ 9.43 (dd, J=1.0 Hz, 6.9 Hz, 1H), 7.92 (dd, J=1.0 Hz, 7.3 Hz, 1H), 7.78-7.76 (m, 2H), 7.44-7.41 (m, 3H), 6.78 (t, J=7.1 Hz, 1H), 4.29 (q, J=7.1 Hz, 2H), 1.20 (t, J=7.1 Hz, 3H); $^{13}$C$^1$H NMR (100 MHz, CDCl$_3$) δ 161.4, 153.8, 146.4, 137.2, 134.3, 130.6, 128.9, 128.5, 127.7, 114.8, 113.9, 84.0, 60.8, 14.0; IR (KBr) 2979, 1685, 1488, 1400, 1320, 1238, 1202, 1163, 1054 cm$^{-1}$; HRMS (EI) calcd for $C_{16}H_{13}N_2O_2I$ 392.0022, found 392.0019.

Example 24

Preparation of ethyl 7-acetyl-2-phenylimidazo[1,2-a]pyridine-3-carboxylate

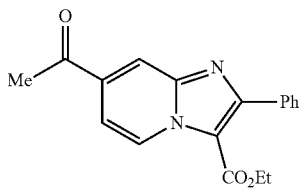 [SMILES: CCOC(=O)c1c(-c2ccccc2)nc2cc(C(C)=O)ccn12]

Cu(hfacac)$_2$ (5.0 mol %), α-diazo oxime ether derivative 7 (0.4 mmol), reaction temperature of 80° C., and reaction time for 3 hours Yield: 58.6 mg (95%); White solid, mp 148-150° C.; $R_f$=0.4 (EtOAc:DCM:Hexane=1:20:20); $^1$H NMR (400 MHz, CDCl$_3$) δ 9.43 (d, J=0.8 Hz, 7.3 Hz, 1H), 8.29 (q, J=0.8 Hz, 1H), 7.79-7.77 (m, 2H), 7.60 (dd, J=1.8 Hz, 7.3 Hz, 1H), 7.47-7.45 (m, 3H), 4.34 (q, J=7.1 Hz, 2H), 2.70 (s, 3H), 1.25 (t, J=7.1 Hz, 3H); $^{13}$C$^1$H NMR (100 MHz, CDCl$_3$) δ 195.8, 161.0, 155.0, 146.2, 135.4, 134.0, 130.3, 129.2, 128.3, 127.8, 119.0, 113.6, 111.7, 61.0, 26.4, 14.1; IR (KBr) 3057, 2988, 2926, 1684, 1403, 1381, 1312, 1231 cm$^{-1}$; HRMS (EI) Calcd for $C_{18}H_{16}N_2O_3$ 308.1161, found 308.1162.

Example 25

Preparation of 3-ethyl 7-methyl 2-phenylimidazo[1,2-a]pyridine-3,7-dicarboxylate

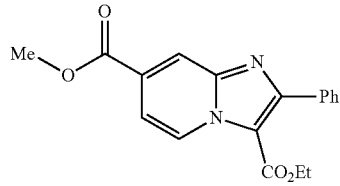 [SMILES: CCOC(=O)c1c(-c2ccccc2)nc2cc(C(=O)OC)ccn12]

Cu(hfacac)$_2$ (5.0 mol %), α-diazo oxime ether derivative 7 (0.4 mmol), reaction temperature of 80° C., and reaction time for 3 hours Yield: 44.1 mg (68%); White solid, mp 123-125° C.; $R_f$=0.2 (EtOAc:DCM:Hexane=1:10:10); $^1$H NMR (400 MHz, CDCl$_3$) d 9.45 (d, J=7.3 Hz, 1H), 8.42 (s, 1H), 7.78-7.76 (m, 2H), 7.62 (dd, J=1.7 Hz, 7.3 Hz, 1H), 7.47-7.43 (m, 3H), 4.33 (q, J=7.1 Hz, 2H), 4.00 (s, 3H), 1.24 (t, J=7.1 Hz, 3H); $^{13}$C$^1$H NMR (100 MHz, CDCl$_3$) d 165.3, 161.0, 155.0, 146.2, 134.1, 130.3, 129.2, 129.1, 128.1, 127.8, 119.8, 113.4, 113.3, 61.0, 52.9, 14.1; IR (KBr) 3136, 3068, 2983, 2953, 1725, 1688, 1489, 1406, 1324 cm$^{-1}$; HRMS (EI) Calcd for $C_{18}H_{16}N_2O_4$ 324.1110, found 324.1107.

Example 26

Preparation of ethyl 7-(2-oxo-2-(2,2,2-trifluoroethoxy)acetyl)-2-phenylimidazo[1,2-a]pyridine-3-carboxylate)

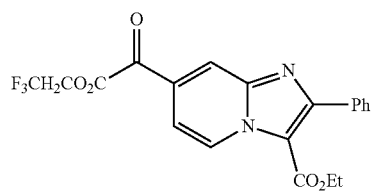

Cu(hfacac)$_2$ (5.0 mol %), α-diazo oxime ether derivative 7 (0.4 mmol), reaction temperature of 80° C., and reaction time for 3 hours Yield: 21.9 mg (26%); Colorless oil; $R_f$=0.3 (EtOAc:DCM:Hexane=1:10:10); $^1$H NMR (400 MHz, CDCl$_3$) d 9.48 (dd, J=0.9 Hz, 7.3 Hz, 1H), 8.50 (q, J=0.9 Hz, 1H), 7.79-7.76 (m, 2H), 7.61 (dd, J=1.8 Hz, 7.3 Hz, 1H), 7.47-7.44 (m, 3H), 4.76 (q, J=8.3 Hz), 4.34 (q, J=7.1 Hz, 2H), 1.24 (t, J=7.1 Hz, 3H); $^{13}$C$^1$H NMR (100 MHz, CDCl$_3$) d 163.3, 160.9, 155.2, 145.9, 133.9, 130.3, 129.2, 128.4, 127.9, 127.2, 123.0 (J=277.2 Hz), 120.6, 113.7, 113.1, 61.5 (J=36.9 Hz), 61.1, 14.1; $^{19}$F NMR δ −73.6 ppm; IR (KBr) 2980, 2931, 2851, 1740, 1689, 1406, 1384, 1227, 1167 cm$^{-1}$; HRMS (EI) Calcd for $C_{19}H_{15}F_3N_2O_4$ 324.1110; found 324.1107.

Example 27

Preparation of ethyl 2-phenylimidazo[1,2-a]quinoline-1-carboxylate

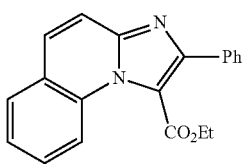 [SMILES: CCOC(=O)c1c(-c2ccccc2)nc2ccc3ccccc3n12]

Cu(hfacac)$_2$ (5.0 mol %), α-diazo oxime ether derivative 7 (0.4 mmol), reaction temperature of 80° C., and reaction time for 3 hours Yield: 53.8 mg (85%); White solid; mp 89-91° C.; $R_f$=0.4 (EtOAc:DCM:Hexane=1:10:10); $^1$H NMR (400 MHz, CDCl$_3$) δ 8.12 (d, J=8.7 Hz, 1H), 7.85-7.81 (m, 3H), 7.70 (d, J=9.3 Hz, 1H), 7.65-7.61 (m, 2H), 7.52-7.40 (m, 4H), 4.38 (q, J=7.1 Hz, 2H), 1.21 (t, J=7.2 Hz, 3H); $^{13}$C$^1$H NMR (100 MHz, CDCl$_3$) δ 163.1, 150.9, 146.0, 134.0, 133.5, 129.8, 129.7, 129.4, 128.8, 128.7, 128.1, 125.4, 124.6, 118.3, 117.0, 116.2, 61.9, 14.0; IR (KBr) 3058, 2979, 1710, 1445, 1370, 1193 cm$^{-1}$; HRMS (EI) calcd for C$_{20}$H$_{16}$N$_2$O$_2$ 316.1212, found 316.1209.

Example 28

Preparation of ethyl 2-phenylimidazo[2,1-a]isoquinoline-3-carboxylate

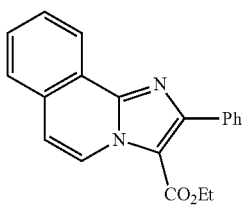 [SMILES: CCOC(=O)c1c(-c2ccccc2)nc2c3ccccc3ccn12]

Cu(hfacac)$_2$ (5.0 mol %), α-diazo oxime ether derivative 7 (0.4 mmol), reaction temperature of 80° C., and reaction time for 3 hours Yield: 51.3 mg (81%); White solid; mp 125-127° C.; $R_f$=0.3 (EtOAc:DCM:Hexane=1:20:20); $^1$H NMR (400 MHz, CDCl$_2$) δ 9.17 (d, J=7.5 Hz, 1H), 8.80 (q, J=3.1 Hz, 1H), 7.82-7.79 (m, 3H), 7.69-7.67 (m, 2H), 7.48-7.42 (m, 3H), 7.27 (d, J=8.7 Hz, 1H), 4.33 (q, J=7.1 Hz, 2H), 1.24 (t, J=7.1 Hz, 3H); $^{13}$C$^1$H NMR (100 MHz, CDCl$_3$) δ 161.4, 152.0, 145.2, 134.8, 130.6, 130.4, 129.6, 128.6, 128.4, 127.8, 126.8, 124.6, 124.5, 123.2, 114.3, 113.8, 60.7, 14.1; IR (KBr) 3134, 3056, 2979, 2904, 1692, 1516, 1400, 1369, 1222, 1163 cm$^{-1}$; HRMS (EI) calcd for C$_{20}$H$_{16}$N$_2$O$_2$ 316.1212, found 316.1209.

Example 29

Preparation of ethyl 2,7-diphenylimidazo[1,2-a]pyridine-3-carboxylate

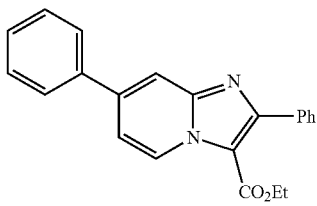 [SMILES: CCOC(=O)c1c(-c2ccccc2)nc2cc(-c3ccccc3)ccn12]

Cu(hfacac)$_2$ (5.0 mol %), α-diazo oxime ether derivative 7 (0.4 mmol), reaction temperature of 80° C., and reaction time for 3 hours Yield: 15.1 mg (22%); White solid; mp 168-170° C.; $R_f$=0.35 (EtOAc:DCM:Hexane=1:20:20); $^1$H NMR (400 MHz, CDCl$_3$) δ 9.44 (dd, J=0.9 Hz, 7.3 Hz, 1H), 7.94 (q, J=0.9 Hz, 1H), 7.81-7.79 (m, 2H), 7.72-7.70 (m, 2H), 7.53-7.49 (m, 2H), 7.47-7.42 (m, 4H), 7.33 (dd, J=1.9 Hz, 7.3 Hz 1H), 4.33 (q, J=8.4 Hz, 2H) 1.24 (t, J=7.1 Hz, 3H); $^{13}$C$^1$H NMR (100 MHz, CDCl$_3$) δ 161.2, 154.4, 147.8, 141.0, 138.1, 134.6, 130.3, 129.4, 129.0, 128.8, 128.3, 127.7, 127.1, 114.2, 113.8, 111.9, 60.6, 14.1; IR (KBr) 3033, 2985, 2904, 1671, 1406, 1381, 1227, 1165, 1049 cm$^{-1}$; HRMS (EI) calcd for C$_{22}$H$_{18}$N$_2$O$_2$ 342.1368, found 342.1370.

Example 30

Preparation of 2,2,2-trifluoroethyl 2,7-diphenylimidazo[1,2-a]pyridine-3-carboxylate

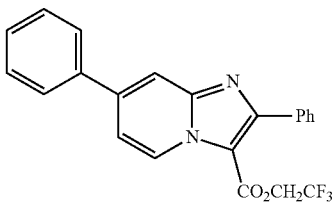

Cu(hfacac)$_2$ (5.0 mol %), α-diazo oxime ether derivative 7 (0.4 mmol), reaction temperature of 80° C., and reaction time for 3 hours Yield: 30.9 mg (39%); White solid; mp 195-197° C.; $R_f$=0.4 (EtOAc:DCM:Hexane=1:20:20); $^1$H NMR (400 MHz, CDCl$_3$) δ 9.40 (dd, J=0.7 Hz, 7.3 Hz, 1H), 7.98 (q, J=0.9 Hz, 1H), 7.77-7.75 (m, 2H), 7.73-7.70 (m, 2H), 7.55-7.51 (m, 2H), 7.48-7.45 (m, 4H), 7.39 (dd, J=1.9 Hz, J=7.3 Hz, 1H), 4.63 (q, J=8.4 Hz, 2H); $^{13}$C$^1$H NMR (100 MHz, CDCl$_3$) δ 159.1, 156.2, 148.5, 141.9, 137.8, 134.0, 130.1, 129.4, 129.2, 129.1, 128.4, 127.9, 127.1, 123.1 (J=277.6 Hz), 114.4, 114.3, 110.3, 59.9 (J=36.9 Hz); $^{19}$F NMR δ −73.1 ppm; IR (KBr) 3033, 2985, 2904, 1671, 1406, 1381, 1227, 1165, 1049 cm$^{-1}$; HRMS (EI) calcd for C$_{22}$H$_{15}$F$_3$N$_2$O$_2$ 396.1086, found 396.1088.

Example 31

Preparation of ethyl 2-phenyl-7-(p-tolyl)imidazo[1,2-a]pyridine-3-carboxylate

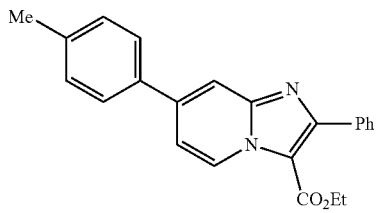 [SMILES: CCOC(=O)c1c(-c2ccccc2)nc2cc(-c3ccc(C)cc3)ccn12]

Cu(hfacac)$_2$ (5.0 mol %), α-diazo oxime ether derivative 7 (0.4 mmol), reaction temperature of 80° C., and reaction time for 3 hours Yield: 14.3 mg (20%); White solid; mp 176-178° C.; R$_f$=0.25 (EtOAc:DCM:Hexane=1:20:20); $^1$H NMR (400 MHz, CDCl$_3$) δ 9.42 (dd, J=0.6 Hz, 7.3 Hz, 1H), 7.92 (q, J=0.9 Hz, 1H), 7.81-7.78 (m, 2H) 7.61 (d, J=8.2 Hz, 2H), 7.45-7.42 (m, 3H), 7.33-7.30 (m, 3H), 4.32 (q, J=7.1 Hz, 2H), 2.43 (s, 3H), 1.24 (t, J=7.1 Hz, 3H); $^{13}$C$^1$H NMR (100 MHz, CDCl$_3$) δ 161.3, 154.4, 147.9, 141.0, 139.1, 135.2, 134.7, 130.3, 130.1, 128.8, 128.3, 127.7, 126.9, 113.8, 111.8, 60.6, 29.8, 21.4, 14.2; IR (KBr) 2988, 2921, 1674, 1382, 1226, 1163, 1050 cm$^{-1}$; HRMS (EI) calcd for C$_{23}$H$_{20}$N$_2$O$_2$ 356.1525, found 356.1522.

Example 32

Preparation of 2,2,2-trifluoroethyl 2-phenyl-7-(p-tolyl)imidazo[1,2-a]pyridine-3-carboxylate

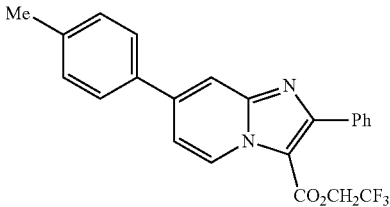

Cu(hfacac)$_2$ (5.0 mol %), α-diazo oxime ether derivative 7 (0.4 mmol), reaction temperature of 80° C., and reaction time for 3 hours Yield: 32.0 mg (39%); White solid; mp 191-193° C.; R$_f$=0.3 (EtOAc:DCM:Hexane=1:20:20); $^1$H NMR (400 MHz, CDCl$_3$) δ 9.37 (d, J=7.3 Hz, 1H), 7.95 (s, 1H), 7.77-7.74 (m, 2H), 7.61 (d, J=8.2 Hz, 2H), 7.47-7.44 (m, 3H), 7.37 (dd, J=1.9 Hz, 7.3 Hz, 1H), 7.33 (q, J=8.0 Hz, 2H), 4.62 (q, J=8.5 Hz, 2H), 2.43 (s, 3H); NMR (100 MHz, CDCl$_3$) δ 159.1, 156.2, 148.6, 141.9, 139.4, 134.9, 134.1, 130.1, 129.2, 128.3, 127.9, 127.2, 126.9, 123.1 (J=277.7 Hz), 114.3, 113.9, 110.2, 59.9 (J=36.9 Hz), 21.4, 1.2; $^{19}$F NMR δ −73.1 ppm; IR (KBr) 2960, 2351, 1675, 1385, 1286, 1176, 1156, 1067 cm$^{-1}$; HRMS (EI) calcd for C$_{23}$H$_{17}$F$_3$N$_2$O$_2$ 410.1242, found 410.1242.

Example 33

Preparation of ethyl 7-(4-chlorophenyl)-2-phenylimidazo[1,2-a]pyridine-3-carboxylate

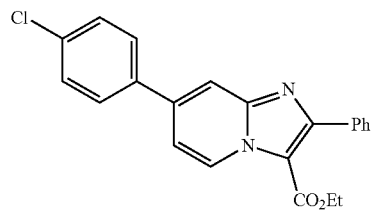 [SMILES: CCOC(=O)c1c(-c2ccccc2)nc2cc(-c3ccc(Cl)cc3)ccn12]

Cu(hfacac)$_2$ (5.0 mol %), α-diazo oxime ether derivative 7 (0.4 mmol), reaction temperature of 80° C., and reaction time for 3 hours Yield: 24.9 mg (33%); White solid; mp 213-215° C.; R$_f$=0.25 (EtOAc:DCM:Hexane=1:20:20); $^1$H NMR (400 MHz, CDCl$_3$) δ 9.45 (dd, J=0.8 Hz, 7.3 Hz, 1H), 7.90 (q, J=0.9 Hz, 1H) 7.80-7.78 (m, 2H), 7.63 (dd, J=1.9 Hz, 6.6 Hz, 2H) 7.50-7.43 (m, 5H), 7.28-7.26 (m, 1H), 4.33 (q, J=7.1 Hz, 2H), 1.24 (t, J=7.1 Hz, 3H); $^{13}$C$^1$H NMR (100 MHz, CDCl$_3$) δ 161.2, 154.5, 147.6, 139.6, 136.6, 135.2, 134.5, 130.3, 129.6, 128.9, 128.5, 128.3, 127.7, 114.2, 113.5, 112.0, 60.7, 14.1; IR (KBr) 3028, 2966, 2925, 2349, 1668, 1488, 1226, 1168 cm$^{-1}$; HRMS (EI) calcd for C$_{22}$H$_{17}$ClN$_2$O$_2$ 376.0979, found 376.0981.

Example 34

Preparation of 2,2,2-trifluoroethyl 7-(4-chlorophenyl)-2-phenylimidazo[1,2-a]pyridine-3-carboxylate

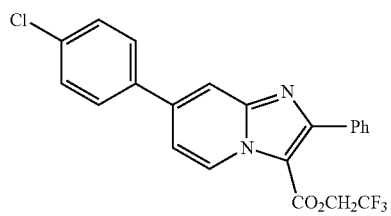

Cu(hfacac)$_2$ (5.0 mol %), α-diazo oxime ether derivative 7 (0.4 mmol), reaction temperature of 80° C., and reaction time for 3 hours Yield: 34.5 mg (40%); White solid; mp 199-201° C.; R$_f$=0.3 (EtOAc:DCM:Hexane=1:20:20); $^1$H NMR (400 MHz, CDCl$_3$) δ 9.40 (d, J=7.2 Hz, 1H), 7.93 (s, 1H), 7.75 (q, J=3.2 Hz, 2H), 7.64 (d, J=8.5 Hz, 2H), 7.50-7.45 (m, 5H), 7.33 (dd, J=1.8 Hz, 7.3 Hz, 1H), 4.63 (q, J=8.4 Hz, 2H); $^{13}$C$^1$H NMR (100 MHz, CDCl$_3$) δ 159.1, 156.3, 148.3, 140.6, 136.3, 135.5, 133.9, 130.1, 129.7, 129.3, 128.6, 128.3, 128.0, 123.0 (J=278.0 Hz), 114.4, 114.0, 110.4, 60.0 (J=36.9 Hz); $^{19}$F NMR δ −73.1 ppm; IR (KBr) 2964, 2920, 1670, 1387, 1290, 1224, 1166, 1068 cm$^{-1}$; HRMS (EI) calcd for C$_{22}$H$_{14}$ClF$_3$N$_2$O$_2$ 430.0696, found 430.0694.

Example 35

Preparation of ethyl 2-phenylimidazo[1,2-b]pyridazine-3-carboxylate

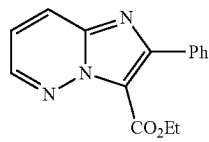 [SMILES: CCOC(=O)c1c(-c2ccccc2)nc2cccnn12]

Cu(hfacac)$_2$ (5.0 mol %), α-diazo oxime ether derivative 7 (0.4 mmol), reaction temperature of 80° C., and reaction time for 3 hours Yield: 42.9 mg (80%); White solid; mp 89-91° C.; R$_f$=0.2 (EtOAc:DCM:Hexane=1:3:3); $^1$H NMR (400 MHz, CDCl$_3$) δ 8.57 (dd, J=1.6 Hz, 4.4 Hz, 1H), 8.05 (dd, J=1.6 Hz, 9.2 Hz, 1H), 7.82-7.80 (m, 2H), 7.49-7.43 (m, 3H), 7.24 (q, J=4.5 Hz, 1H), 4.40 (q, J=7.1 Hz, 2H), 1.27 (t, J=7.1 Hz, 3H); $^{13}$C$^1$H NMR (100 MHz, CDCl$_3$) δ 159.9, 151.2, 144.0, 140.7, 133.8, 129.8, 129.1, 128.0, 125.7, 119.4, 116.9, 61.2, 14.1; IR (KBr) 2980, 2917, 1714, 1531, 1485, 1415, 1329, 1279, 1183 cm$^{-1}$; HRMS (EI) calcd for C$_{15}$H$_{13}$N$_3$O$_2$ 267.1008, found 267.1006.

Example 36

Preparation of ethyl 6-methyl-2-phenylimidazo[1,2-b]pyridazine-3-carboxylate

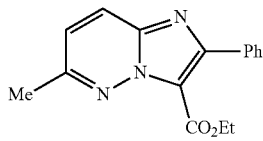 [SMILES: CCOC(=O)c1c(-c2ccccc2)nc2ccc(C)nn12]

Cu(hfacac)$_2$ (5.0 mol %), α-diazo oxime ether derivative 7 (0.4 mmol), reaction temperature of 80° C., and reaction time for 3 hours Yield: 54.0 mg (96%); White solid; mp 107-109° C.; R$_f$=0.3 (EtOAc:DCM:Hexane=1:3:3); $^1$H NMR (400 MHz, CDCl$_3$) δ 7.91 (d, J=9.2 Hz, 1H), 7.80-7.78 (m, 2H), 7.46-7.42 (m, 3H), 7.10 (d, J=9.3 Hz, 1H), 4.38 (q, J=7.1 Hz, 2H), 2.69 (s, 3H), 1.27 (t, J=7.1 Hz, 3H); $^{13}$C$^1$H NMR (100 MHz, CDCl$_3$) δ 160.1, 153.2, 150.6, 139.8, 134.0, 129.8, 128.9, 128.0, 125.2, 121.5, 116.8, 61.1, 22.3, 14.1; IR (KBr) 2981, 1715, 1616, 1547, 1338 cm$^{-1}$; HRMS (EI) calcd for C$_{16}$H$_{15}$N$_3$O$_2$ 281.1164, found 281.1162.

Example 37

Preparation of ethyl 7-methyl-2-phenylimidazo[1,2-c]pyridine-3-carboxylate

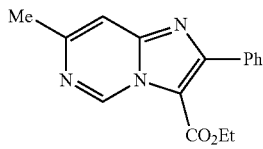

Cu(hfacac)$_2$ (10.0 mol %), α-diazo oxime ether derivative 7 (0.5 mmol), reaction temperature of 80° C., and reaction time for 12 hours Yield: 30.4 mg (54%); White solid; mp 73-76° C.; R$_f$=0.3 (EtOAc:DCM:Hexane=1:3:3); $^1$H NMR (400 MHz, CDCl$_3$) δ 10.05 (d, J=1.1 Hz, 1H), 7.81-7.78 (m, 2H), 7.46-7.42 (m, 4H), 4.35 (q, J=7.1 Hz, 2H), 2.62 (d, J=0.4 Hz, 3H), 1.27 (t, J=7.1 Hz, 3H); $^{13}$C$^1$H NMR (100 MHz, CDCl$_3$) δ 160.6, 154.8, 152.9, 147.9, 140.4, 133.5, 130.4, 129.4, 127.8, 110.8, 109.9, 61.1, 23.9, 14.1; IR (KBr) 2980, 1758, 1685, 1580, 1334 cm$^{-1}$; HRMS (EI) calcd for C$_{16}$H$_{15}$N$_3$O$_2$ 281.1164, found 281.1162.

Example 38

Preparation of ethyl 2-phenylimidazo[1,2-a]pyrazine-3-carboxylate

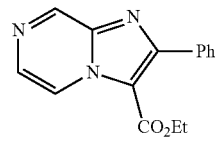 [SMILES: CCOC(=O)c1c(-c2ccccc2)nc2cnccn12]

Cu(hfacac)$_2$ (5.0 mol %), α-diazo oxime ether derivative 7 (0.4 mmol), reaction temperature of 80° C., and reaction time for 3 hours Yield: 28.4 mg (53%), White solid; mp 89-91° C.; R$_f$=0.3 (EtOAc:Hexane=1:2); $^1$H NMR (400 MHz, CDCl$_3$) δ 9.25-9.23 (m, 2H), 8.15 (d, J=4.6 Hz, 1H), 7.81-7.78 (m, 2H), 7.47-7.46 (m, 3H), 4.37 (q, J=7.1 Hz, 2H), 1.27 (t, J=7.1 Hz, 3H); $^{13}$C$^1$H NMR (100 MHz, CDCl$_3$) δ 160.7, 154.1, 143.9, 141.5, 133.5, 131.8, 130.4, 129.4, 127.9, 120.7, 113.2, 61.3, 14.1; IR (KBr) 3138, 3065, 2992, 1685, 1487, 1474, 1402, 1383, 1254, 1209, 1164 cm$^{-1}$; HRMS (EI) calcd for C$_{15}$H$_{13}$N$_3$O$_2$ 267.1008, found 267.1006.

Example 39

Preparation of ethyl 8-methyl-2-phenylimidazo[1,2-a]pyrazine-3-carboxylate

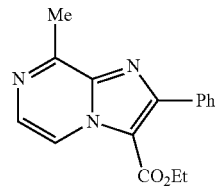 [SMILES: CCOC(=O)c1c(-c2ccccc2)nc2c(C)nccn12]

Cu(hfacac)$_2$ (5.0 mol %), α-diazo oxime ether derivative 7 (0.4 mmol), reaction temperature of 80° C., and reaction time for 3 hours Yield: 33.1 mg (59%); White solid; mp 130-132° C.; R$_f$=0.3 (EtOAc:DCM:Hexane=1:3:3); $^1$H NMR (400 MHz, CDCl$_3$) δ 9.10 (d, J=4.7 Hz, 1H), 8.00 (d, J=4.7 Hz, 1H), 7.78-7.76 (m, 2H), 7.47-7.44 (m, 3H), 4.34 (q, J=7.1 Hz, 2H), 2.97 (s, 3H) 1.24 (t, J=7.1 Hz, 3H); $^{13}$C$^1$H NMR (100 MHz, CDCl$_3$) δ 160.8, 153.3, 153.2, 141.2, 133.9, 131.1, 130.4, 129.2, 127.9, 119.1, 113.6, 61.2, 20.9, 14.1; IR (KBr) 2997, 2983, 1684, 1481, 1409, 1257, 1168 cm$^{-1}$; HRMS (EI) calcd for C$_{16}$H$_{15}$N$_3$O$_2$ 281.1164, found 281.1162.

Example 40

Preparation of ethyl 6,8-dimethyl-2-phenylimidazo[1,2-a]pyrazine-3-carboxylate

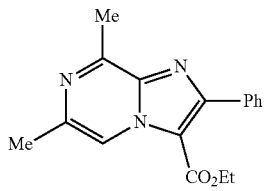 [SMILES: CCOC(=O)c1c(-c2ccccc2)nc2c(C)nc(C)cn12]

Cu(hfacac)$_2$ (5.0 mol %), α-diazo oxime ether derivative 7 (0.4 mmol), reaction temperature of 80° C., and reaction time for 3 hours Yield: 41.9 mg (71%); Yellow solid; mp 128-130° C.; R$_f$=0.2 (EtOAc:DCM:Hexane=1:5:5); $^1$H NMR (400 MHz, CDCl$_3$) δ 8.96 (s, 1H), 7.76-7.74 (m, 2H), 7.46-7.43 (m, 3H), 4.32 (q, J=7.1 Hz, 2H), 2.95 (s, 3H), 2.58 (s, 3H), 1.23 (t, J=7.1 Hz, 3H); $^{13}$C$^1$H NMR (100 MHz, CDCl$_3$) δ 161.0, 153.3, 151.9, 140.1, 134.2, 130.3 (2C), 129.0, 127.8 (2C), 116.2, 61.0, 21.4, 20.8, 14.1; IR (KBr) 2981, 2925, 1690, 1488, 1406, 1379, 1290, 1171, 1132 cm$^{-1}$; HRMS (EI) calcd for C$_{17}$H$_{17}$N$_3$O$_2$ 295.1321, found 295.1319.

Example 41

Preparation of ethyl 6,8-dimethyl-2-phenylimidazo[1,2-a]pyridine-3-carboxylate

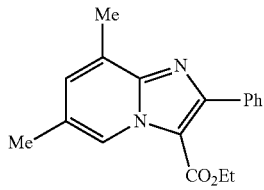 [SMILES: CCOC(=O)c1c(-c2ccccc2)nc2c(C)cc(C)cn12]

Cu(hfacac)$_2$ (5.0 mol %), α-diazo oxime ether derivative 7 (0.4 mmol), reaction temperature of 80° C., and reaction time for 3 hours Yield: 6.0 mg (10%); White solid; R$_f$=0.2 (EtOAc:DCM:Hexane=1:20:20); $^1$H NMR (400 MHz, CDCl$_3$) δ 9.10 (br s, 1H), 7.74-7.71 (m, 2H), 7.43-7.38 (m, 3H), 7.10 (br s, 1H), 4.26 (q, J=7.1 Hz, 2H), 2.65 (s, 3H), 2.38 (d, J=0.7 Hz, 3H), 1.18 (t, J=7.1 Hz, 3H).

Example 42

Preparation of 2,2,2-trifluoroethyl 6,8-dimethyl-2-phenylimidazo[1,2-a]pyridine-3-carboxylate

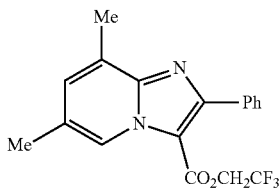

Cu(hfacac)$_2$ (5.0 mol %), α-diazo oxime ether derivative 7 (0.4 mmol), reaction temperature of 80° C., and reaction time for 3 hours Yield: 19.5 mg (28%); White solid; R$_f$=0.3 (EtOAc:DCM:Hexane=1:20:20); $^1$H NMR (400 MHz, CDCl$_3$) δ 9.04 (br s, 1H), 7.71-7.68 (m, 2H), 7.45-7.40 (m, 3H), 7.16 (br s, 1H), 4.58 (q, J=8.5 Hz, 2H), 2.66 (s, 3H), 2.40 (s, 3H).

Example 43

Preparation of ethyl 8-bromo-2-methylimidazo[1,2-a]pyridine-3-carboxylate

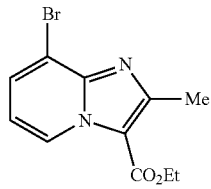

Cu(hfacac)$_2$ (5.0 mol %), α-diazo oxime ether derivative 7 (0.4 mmol), reaction temperature of 80° C., and reaction time for 3 hours Yield: 30.0 mg (53%); White solid; R$_f$=0.2 (EtOAc:DCM:Hexane=1:20:20); $^1$H NMR (400 MHz, CDCl$_3$) δ 9.33 (dd, J=0.8 Hz, 6.9 Hz, 1H), 7.63 (dd, J=0.8 Hz, 7.4 Hz, 1H), 6.86 (t, J=7.2 Hz, 1H), 4.44 (q, J=7.1 Hz, 2H), 2.77 (s, 3H), 1.45 (t, J=7.1 Hz, 3H).

Example 44

Preparation of 2,2,2-trifluoroethyl 8-(benzyloxy)-2-methylimidazo[1,2-a]pyridine-3-carboxylate

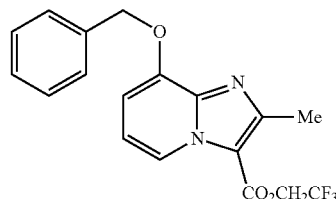

Cu(hfacac)$_2$ (5.0 mol %), α-diazo oxime ether derivative 7 (0.4 mmol), reaction temperature of 80° C., and reaction time for 3 hours Yield: 21.9 mg (30%); White solid; R$_f$=0.2 (EtOAc:DCM:Hexane=1:20:20); $^1$H NMR (400 MHz, CDCl$_3$) δ 8.84 (d, J=6.8 Hz, 1H), 7.45 (d, J=7.5 Hz, 2H), 7.39-7.32 (m, 3H), 6.84 (t, J=7.2 Hz, 1H), 6.73 (d, J=7.8 Hz, 1H), 5.38 (s, 2H), 4.74 (q, J=8.4 Hz, 2H), 2.80 (s, 3H).

Example 45

Preparation of ethyl 2-phenylimidazo[1,2-c]pyrimidine-3-carboxylate

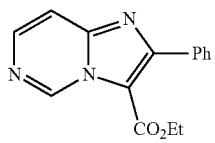 [SMILES: CCOC(=O)c1c(-c2ccccc2)nc2ccncn12]

Cu(hfacac)₂ (5.0 mol %), α-diazo oxime ether derivative 7 (0.4 mmol), reaction temperature of 80° C., and reaction time for 3 hours Yield: 17.2 mg (32%); White solid; R_f=0.2 (EtOAc:DCM:Hexane=1:20:20); ¹H NMR (400 MHz, CDCl₃) δ 10.16 (d, J=1.4 Hz, 1H), 8.18 (d, J=6.3 Hz, 1H), 7.82-7.79 (m, 2H), 7.64 (dd, J=1.4 Hz, 6.3 Hz, 1H), 7.47-7.45 (m, 3H), 4.37 (q, J=7.1 Hz, 2H), 1.28 (t, J=7.1 Hz, 3H).

Example 46

Preparation of ethyl 8-bromo-2-phenylimidazo[1,2-c]pyrimidine-3-carboxylate

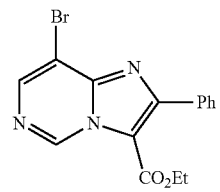

Cu(hfacac)₂ (5.0 mol %), α-diazo oxime ether derivative 7 (0.4 mmol), reaction temperature of 80° C., and reaction time for 3 hours Yield: 24.2 mg (35%); White solid; R_f=0.2 (EtOAc:DCM:Hexane=1:20:20); ¹H NMR (400 MHz, CDCl₃) δ 10.10 (s, 1H), 8.35 (s, 1H), 7.82-7.79 (m, 2H), 7.47-7.44 (m, 3H), 7.47-7.45 (m, 3H), 4.36 (q, J=7.1 Hz, 2H), 1.26 (t, J=7.1 Hz, 3H).

Example 47

Preparation of 2,2,2-trifluoroethyl 2-(4-chlorophenyl)imidazo[1,2-c]pyrimidine-3-carboxylate

Cu(hfacac)₂ (5.0 mol %), α-diazo oxime ether derivative 7 (0.4 mmol), reaction temperature of 80° C., and reaction time for 3 hours Yield: 23.5 mg (33%); White solid; R_f=0.2 (EtOAc:DCM:Hexane=1:20:20); ¹H NMR (400 MHz, CDCl₃) δ 10.15 (s, 1H), 8.18 (d, J=6.3 Hz, 1H), 7.77 (d, J=8.4 Hz, 2H), 7.63 (d, J=5.8 Hz, 1H), 7.44 (d, J=6.3 Hz, 2H), 4.39 (q, J=7.1 Hz, 2H), 1.31 (t, J=7.1 Hz, 3H).

Example 48

Preparation of Saripidem

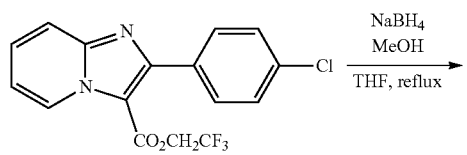

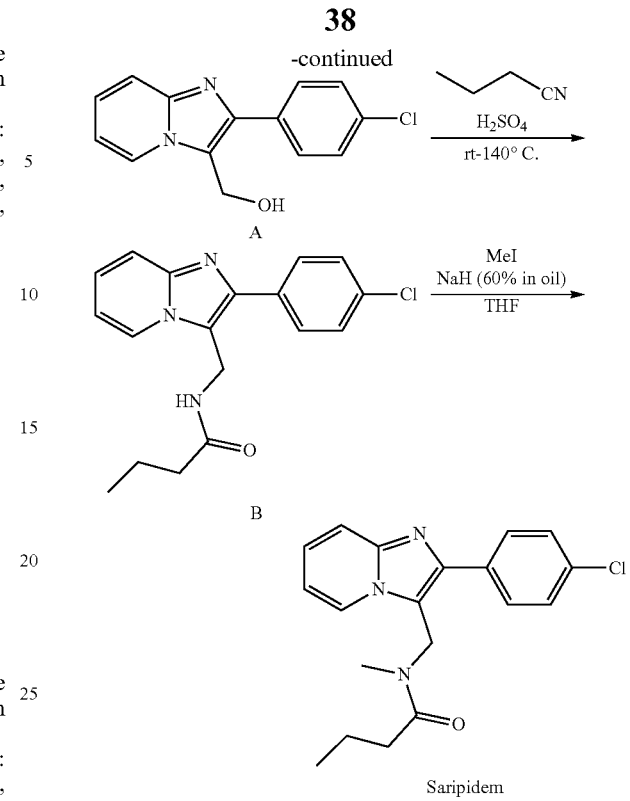

Preparation of 2-(4-chlorophenyl)imidazo[1,2-a]pyridine-3-yl)methanol (Compound A)

2,2,2-trifluoroethyl 2-(4-chlorophenyl)imidazo[1,2-a]pyridine-3-carboxylate (66.6 mg, 0.2 mmol) prepared in Example 12 was added to THF (0.5 mL), fine powdered NaBH₄ (43.9 mg, 1.16 mmol) was added while refluxing, and the mixture was stirred for 15 minutes. Methanol (0.4 mL) was added dropwise over 15 minutes, then the reaction mixture was stirred and refluxed for 1 hour. After confirming that the starting material disappeared completely through TLC, the reaction was terminated. The reaction mixture was cooled to room temperature and quenched with saturated aqueous NH₄Cl solution (0.63 mL). The organic layer was then separated and the water layer was extracted with EtOAc. The combined organic layer was dried over anhydrous MgSO₄ and concentrated under reduced pressure to obtain (2-(4-chlorophenyl)imidazo[1,2-a]pyridine-3-yl)methanol (Compound A) (48.0 mg, 93%).

White solid; ¹H NMR (400 MHz, DMSO) δ 8.48 (d, J=6.8 Hz, 1H), 7.88 (d, J=8.5 Hz, 2H), 7.63 (d, J=9.0 Hz, 1H), 7.57 (d, J=8.5 Hz, 2H), 7.34 (t, J=7.8 Hz, 1H), 7.01 (t, J=6.8 Hz, 1H), 5.44 (t, J=5.2 Hz, 1H) 4.92 (d, J=5.2 Hz, 2H).

Preparation of N-((2-(4-chlorophenyl)imidazo[1,2-a]pyridine-3-yl)methyl)butyramide (Compound B)

(2-(4-chlorophenyl)imidazo[1,2-a]pyridine-3-yl)methanol (Compound A, 51.7 mg, 0.2 mmol) was suspended in butyronitrile (0.45 mL), and then H₂SO₄ (0.054 mL) was slowly added dropwise. The reaction mixture was stirred at room temperature for 1.5 hours and then heated at 140° C. for 30 minutes. Then, the reaction mixture was cooled to room temperature, the supernatant was removed, and the lower phase was treated with ice. After the gum was completely dissolved, the solution was treated with excess NH$_4$OH until a strong basic pH was reached. The insoluble material were extracted with CH$_2$Cl$_2$ and purified by recrystallization (hexane and EtOAc) to obtain N-((2-(4-chlorophenyl)imidazo[1,2-a]pyridine-3-yl)methyl)butyramide (Compound B) (55.7 mg, 85%).

White solid; $^1$H NMR (400 MHz, CDCl$_3$) δ 8.25 (d, J=6.8 Hz, 1H), 7.67-7.62 (m, 3H), 7.45 (d, J=8.5 Hz, 2H), 7.28-7.24 (m, 1H), 6.89-6.86 (m, 1H), 5.61 (s, 1H), 4.96 (d, J=5.6 Hz, 2H), 2.20 (t, J=7.4 Hz, 2H), 1.69 (m, J=7.4 Hz, 2H), 0.94 (t, J=7.4 Hz, 3H).

Preparation of N-((2-(4-chlorophenyl)imidazo[1,2-a]pyridine-3-yl)methyl)-N-methylbutyramide (Saripidem)

A mixed solution of N-((2-(4-chlorophenyl)imidazo[1,2-a]pyridine-3-yl)methyl)butyramide (Compound B, 55.7 mg, 0.17 mmol) and THF (0.51 mL) was added to a suspension of sodium hydride (60% in mineral oil) (14.88 mg, 0.80 mmol) in THF (0.25 mL) containing CH$_3$I (0.016 mL). The reaction mixture was diluted with THF (0.39 mL) and stirred for 2 hours, then methanol (0.017 mL) was added thereto, and the mixture was concentrated under reduced pressure. The residue was treated with water and the insoluble material was extracted with CH$_2$Cl$_2$. The organic phase was dried over anhydrous MgSO$_4$ and the solvent was removed under reduced pressure. The obtained solid was recrystallized with ether to obtain the target compound Saripidem (55.4 mg, 95%).

White solid; $^1$H NMR (400 MHz, CDCl$_3$) δ 8.40 (d, J=6.9 Hz, 1H), 7.70-7.66 (m, 3H), 7.46 (d, J=8.4 Hz, 2H), 7.26 (t, J=7.9 Hz, 1H), 6.85 (t, J=6.8 Hz, 1H), 5.18 (s, 2H), 2.60 (s, 3H), 2.28 (t, J=7.4 Hz, 2H), 1.68 (m, J=7.3 Hz, 2H), 0.96 (t, J=7.4 Hz, 3H).

The imidazo[1,2-a]pyridine-3-carboxylate derivative according to embodiments of the present invention may exhibit physiological activity and pharmacological activity to be effectively used as important raw materials or intermediates in fields of medicine, agricultural chemicals, or the like, such as natural products or chiral auxiliaries, ligands used in asymmetric synthesis, antimicrobial agents, kinase inhibitors, H$_1$-receptor antagonists, anticancer drugs, and the like.

Further, the preparation method of the imidazo[1,2-a]pyridine-3-carboxylate derivative according to embodiments of the present invention is able to efficiently prepare the imidazo[1,2-a]pyridine-3-carboxylate derivative through a simple experimental procedure by performing an aza-[3+2] cycloaddition reaction of a pyridine derivative with an α-diazo oxime ether derivative in the presence of a copper (II) catalyst, and is able to synthesis a wide range of N-heterobicyclic derivatives such as imidazopyridazine, imidazopyrimidine and imidazopyrazine having an α-imino Cu-carbenoid produced from the α-diazo oxime ether derivative and the copper (II) catalyst.

What is claimed is:
1. A preparation method of an imidazo[1,2-a]pyridine-3-carboxylate derivative comprising:
performing an aza-[3+2] cycloaddition reaction of a pyridine derivative represented by Chemical Formula 6 below with an α-diazo oxime ether derivative represented by Chemical Formula 7 below in the presence of a copper (II) catalyst, thereby preparing an imidazo[1,2-a]pyridine-3-carboxylate derivative represented by Chemical Formula 1 below:

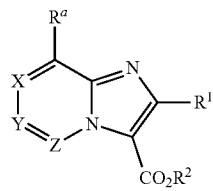

[Chemical Formula 1]

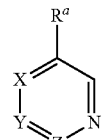

[Chemical Formula 6]

[Chemical Formula 7]

in Chemical Formulas 1, 6, and 7,
R$^1$ is (C1-C10)alkyl, (C6-C12)aryl or (C3-C12)heteroaryl, and the aryl of R$^1$ may be further substituted with one or more selected from the group consisting of (C1-C10)alkyl, halo(C1-C10)alkyl, (C1-C10)alkoxy, halogen, nitro, (C1-C10)alkylcarbonyl, (C1-C10)alkoxycarbonyl and (C6-C12)aryloxy;
R$^2$ is (C1-C10)alkyl or halo(C1-C10)alkyl;
R$^3$ is (C1-C10)alkoxy;
X is CR$^b$ or N;
Y is CR$^c$ or N;
Z is CR$^d$ or N;
R$^a$ to R$^d$ are each independently hydrogen, (C1-C10)alkyl, halo(C1-C10)alkyl, halogen, (C1-C10)alkylcarbonyl, halo(C1-C10)alkylcarbonyl, (C1-C10)alkoxycarbonyl, halo(C1-C10)alkoxycarbonyl, (C6-C12)aryl (C1-C10)alkyloxy, (C6-C12)aryl or (C3-C12) heteroaryl, or may be linked to an adjacent substituent via —CR$^{11}$═CR$^{12}$—CR$^{13}$═CR$^{14}$— to form a fused ring, and the aryl of R$^a$ to R$^d$ may be further substituted with one or more selected from (C1-C10)alkyl, halo (C1-C10)alkyl, (C1-C10)alkoxy, (C6-C12)aryl and halogen;
R$^{11}$ to R$^{14}$ are each independently hydrogen, (C1-C10) alkyl, halo(C1-C10)alkyl, (C1-C10)alkoxy, (C6-C12) aryl, or halogen; and
the heteroaryl includes one to four heteroatoms selected from N, O and S.
2. The preparation method of claim 1, wherein the copper (II) catalyst is one or two or more selected from the group consisting of Cu(OAc)$_2$[Copper(II) acetate], Cu(OTf)$_2$[Copper(II) triflate], Cu(acac)$_2$[Copper(II) acetylacetonate], Cu(tfacac)$_2$[Copper(II) trifluoroacetylacetonate] and Cu(hfacac)$_2$[Copper(II) hexafluoroacetylacetonate].
3. The preparation method of claim 1, wherein the α-diazo oxime ether derivative represented by Chemical Formula 7 is used in an amount of 1 to 3 equivalents with respect to the pyridine derivative represented by Chemical Formula 6.
4. The preparation method of claim 1, wherein the copper (II) catalyst is used in an amount of 1 to 20 mol % with respect to the pyridine derivative represented by Chemical Formula 6.
5. The preparation method of claim 1, wherein the reaction is performed in the presence of one or two or more organic solvents selected from trifluoroethanol, 1,4-dioxane, acetonitrile, toluene, tetrahydrofuran, dimethylformamide, dichloromethane, dichloroethane, N,N-dimethylformamide, hexane, benzene, xylene, chlorobenzene, hexafluorobenzene, octafluorotoluene, tetrabutylalcohol, methanol and ethanol.

6. A preparation method of an imidazo[1,2-a]pyridine-3-carboxylate derivative comprising:
performing an aza-[3+2] cycloaddition reaction of a pyridine derivative represented by Chemical Formula 6A below with an α-diazo oxime ether derivative represented by Chemical Formula 7A below in the presence of a copper (II) catalyst in trifluoroethanol, followed by transesterification with trifluoroethanol as a solvent, thereby preparing an imidazo[1,2-a]pyridine-3-carboxylate derivative represented by Chemical Formula 1A below:

[Chemical Formula 1A]

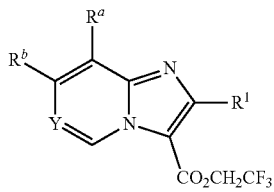

[Chemical Formula 6A]

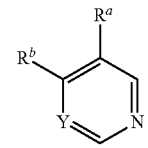

[Chemical Formula 7A]

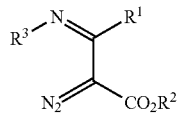

in Chemical Formulas 1A, 6A, and 7A, $R^1$ is (C1-C10)alkyl or (C6-C12)aryl, and the aryl of $R^1$ may be further substituted with one or more selected from the group consisting of (C1-C10)alkyl, (C1-C10)alkoxy, halogen, nitro and (C1-C10)alkoxycarbonyl;

$R^2$ is (C1-C10)alkyl;

Y is $CR^c$ or N;

$R^3$ is (C1-C10)alkoxy;

$R^a$ is hydrogen, (C1-C10)alkyl or (C6-C12)aryl(C1-C10)alkyloxy;

$R^b$ is (C1-C10)alkyl or (C6-C12)aryl, and the aryl of $R^b$ may be further substituted with one or more selected from (C1-C10)alkyl and halogen; and $R^c$ is hydrogen or (C1-C10)alkyl.

7. The preparation method of claim 6, wherein the copper (II) catalyst is one or two or more selected from the group consisting of Cu(OAc)$_2$[Copper(II) acetate], Cu(OTf)$_2$[Copper(II) triflate], Cu(acac)$_2$[Copper(II) acetylacetonate], Cu(tfacac)$_2$[Copper(II) trifluoroacetylacetonate], and Cu(hfacac)$_2$[Copper(II) hexafluoroacetylacetonate].

8. The preparation method of claim 6, wherein the α-diazo oxime ether derivative represented by Chemical Formula 7A is used in an amount of 1 to 3 equivalents with respect to the pyridine derivative represented by Chemical Formula 6A.

9. The preparation method of claim 6, wherein the copper (II) catalyst is used in an amount of 1 to 20 mol % with respect to the pyridine derivative represented by Chemical Formula 6A.

* * * * *